United States Patent [19]
Lupton et al.

[11] Patent Number: 5,874,556
[45] Date of Patent: Feb. 23, 1999

[54] HYBRID GENES FOR USE IN THE PRODUCTION OF $T_H$-INDEPENDENT CYTOTOXIC T CELLS

[75] Inventors: Stephen D. Lupton; James M. Allen, both of Seattle; Andrew L. Feldhaus, Lynwood, all of Wash.

[73] Assignee: Targeted Genetics Corporation, Seattle, Wash.

[21] Appl. No.: 244,548

[22] PCT Filed: Apr. 4, 1994

[86] PCT No.: PCT/US94/03659

§ 371 Date: Jun. 6, 1994

§ 102(e) Date: Jun. 6, 1994

[87] PCT Pub. No.: WO94/22489

PCT Pub. Date: Oct. 13, 1994

Related U.S. Application Data

[63] Continuation-in-part of Ser. No. 44,539, Apr. 6, 1993, abandoned.

[51] Int. Cl.$^6$ .......................... C12N 15/00; C12N 15/24; C12N 15/87; A61K 48/00
[52] U.S. Cl. ..................... 536/23.1; 536/234; 536/23.52; 435/69.1; 435/69.5; 435/69.52; 435/320.1; 435/697; 435/252.3; 435/372.3; 435/372; 435/366; 435/363; 514/44; 424/93 R; 424/93 A; 424/93 B; 424/93 U; 424/93 V
[58] Field of Search ...................... 435/69.1, 69.5–69.52, 435/69.7, 240.2, 320.1; 536/23.1, 23.4, 23.52; 514/44; 424/93 R, 93 A, 93 B, 93 U, 93 V

[56] References Cited

U.S. PATENT DOCUMENTS

| | | | |
|---|---|---|---|
| 5,272,082 | 12/1993 | Santoli et al. | 435/240.2 |
| 5,470,730 | 11/1995 | Greenberg et al. | 435/172.3 |

FOREIGN PATENT DOCUMENTS 9507358  3/1995  WIPO .

OTHER PUBLICATIONS

Karasuyama et al., *J. Exp Med.* 169, 1989, pp. 13–25.
Ullman et al., *Ann Rev. Immunol*, Aug., 1990, pp. 421–452.
Sporn et al., *Ann. Internal Med* 117(5) 1992, pp. 408–414.
Merz et al., *Am. J Pathology* 139(5), 1991, pp. 1173–1188.
Ciavarra, *Cell Immunol* 134(2) 1991, pp. 427–441 (Chem Abst).
Ouerell et al., *Mol Cell Biol* 11(3) 1991, pp. 1590–1597 (Chem Abst).
Abken et al., *Verh Dtsch Ges. Pathol* 74, 1990 pp. 381–385 (Chem Abst).
Greenberg. P.D., "Adoptive T cell therapy of tumors: mechanisms operative in the recognition and elimination of tumor cells" *Advances in Immunology*, Academic Press, Inc., (1991) pp. 280–355.
Cheever et al., "Augmentation of the anti–tumor therapeutic efficacy of long–term cultured T lymphocytes by in vivo administration of purified interleukin 2" *J. Exp. Med.* (1977) 155:968–980.
Alderson et al., "Interleukin 7 enhances cytolytic T lymphocyte generation and induces lymphokine–activated killer cells from human peripheral blood" *J. Exp. Med.* (1990) 172:577–587.
Klarnet et al., "Helper–independent CD8$^+$ cytotoxic T lymphocytes express IL–1 receptors and require IL–2" *J. Immunol.* (1989) 142(7):2187–2191.
Izuhara et al., "The chimeric receptor between interleukin–2 receptor β chain and interleukin–4 receptor transduces interleukin–2 signal" *Biochemical and Biophysical Research Communications* (1993) 190:992–1000.
Kus et al., *Blood* 82(3) 1993, pp. 845–852.
Jiner et al., *Blood* 83(1) 1994, pp. 43–50.
Bodine et al. *PNAS* 86, 1989, pp. 8897–8901.
Culver et al. *PNAS* 88, 1991, pp. 3155–3159.
Kasid et al. *PNAS* 87, 1990, pp. 473–477.

*Primary Examiner*—Garnette D. Draper
*Attorney, Agent, or Firm*—Morrison & Foerster LLP; Tyler M. Dylan

[57] ABSTRACT

Recombinant vectors are provided that render the proliferative response of activated lymphocytes, particularly cytotoxic T lymphocytes, of lessened dependency on T-helper cells. The vectors are comprised of a region encoding a stimulatory factor polypeptide operably linked to a heterologous transcriptional control region. Expression of the stimulatory factor polypeptide from the recombinant polynucleotide in an activated lymphocyte renders the proliferative response of less dependent on lymphocyte T-helper cells. When the lymphocyte is activated by binding of its cognate antigen the transcriptional control region causes transcription of the stimulatory factor encoding region. The cells containing the vector, particularly CTLs, are of use in immunotherapy.

18 Claims, 23 Drawing Sheets

STRUCTURE OF VECTORS

HyTK/hIL-4/CAT

HyTK/hIL-3/CAT

STRUCTURE OF NON-VIRAL VECTORS

TCR = Transcriptional control region hGH = Segment from human growth hormone gene, providing an intron and polyadenylation signal sequence LTR = Long terminal repeat TCR = Transcriptional control region hGH = Segment from the human growth hormone gene encoding exons 4 and 5, and providing an intron and a polyadenylation sequence

STRUCTURE OF AAV VECTORS

Without selectable marker:

ITR = Adenoassociated virus <u>I</u>nverted <u>T</u>erminal <u>R</u>epeat

TCR = Transcriptional control region
(the antigen-regulated one)

hGH = Segment from human growth hormone gene,
providing an intron and polyadenylation signal

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CACACACAAG CTTGCCACCC ACCAGGACCA AGCAGGGCGG GC                42

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACACACACGG ATCCGCAGGA GGCACTCTGT CTTGTTCTG                   39

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CACACACAAG CTTCAATAAA AAACAAGCAG GGCGCGTGGT                   40

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACACACACGG ATCCATTTGC AGTGACAATG TGAGGCAATT AGT               43

( 2 ) INFORMATION FOR SEQ ID NO:5:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TCGAGGGCTC AGAGGGAACC CAGTCAGGAG CTTGAATCCC ACGATTCGGG        50

( 2 ) INFORMATION FOR SEQ ID NO:6:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATCCCCGAA TCGTGGGATT CAAGCTCCTG ACTGGGTTCC CTCTGAGCCC        50

( 2 ) INFORMATION FOR SEQ ID NO:7:

( i ) SEQUENCE CHARACTERISTICS:

(A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:7:

CACACAAAGC TTCTCGAAAC TTCCTTTGTA GA                32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

CACACAGGAT CCGGAGAGCC TCACCTGCTG TG                32

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:9:

CACACACAAG CTTATCGATG ATCTCGAGGA GCTTGCCATT GC     42

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:10:

ACACACACAA GCTTAGACCT CCCACCGTAC ACGCCTAC          38

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:11:

CACACAAAGC TTGACTCCTG AGGACGTTAC AG                32

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:12:

CACACAGGAT CCGGGCTGTC ACCCTTGTGG GT                32

(2) INFORMATION FOR SEQ ID NO:13:

(i) SEQUENCE CHARACTERISTICS:
        (A) LENGTH: 40 base pairs
        (B) TYPE: nucleic acid (C) STRANDEDNESS: single
(D) TOPOLOGY: linear (xi) SEQUENCE DESCRIPTION: SEQ ID NO:13:

CACACACAAG CTTCTATATT TTGAGATATA CCATTCCTCA                40

(2) INFORMATION FOR SEQ ID NO:14:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:14:

ACACACACGG ATCCAGGAAG GCTGCCCTGG TTGGAGCTGC T              41

HYBRID GENES FOR USE IN THE PRODUCTION OF T$_H$-INDEPENDENT CYTOTOXIC T CELLS

CROSS-REFERENCE TO RELATED APPLICATIONS

This application is the U.S. national phase of International application PCT/US94/03659, filed Apr. 4, 1994; which is continuation-in-part of U.S. Ser. No. 08/044,539, filed Apr. 6, 1993, abandoned.

TECHNICAL FIELD

The invention relates to materials for use in immunotherapy, and more specifically to lymphocytes containing recombinant genes that when expressed, enhance growth or proliferation.

BACKGROUND

T lymphocytes are responsible primarily for protection against intracellular pathogens and malignancies. Individuals who are grossly deficient in T-cell immunity frequently succumb to overwhelming infections by organisms such as cytomegalovirus, Pneumocystis carinii, Candida, and other apparently "opportunistic" pathogens, including bacteria, viruses and fungi. These individuals may also succumb to malignancies such as B cell lymphomas, indicating the importance of T cell immunity in the suppression or elimination of certain tumors. Immunosuppression can result from a variety of causes, including viral infections (for example, with the RIV virus), as a result of chemical therapy, and malignancies (particularly of types that affect the hematopoietic system).

All mature T lymphocytes express the CD3 cell surface molecule, but consist of two basic subtypes based on their mutually exclusive expression of cell surface molecules CD4 and CD8. The functional distinction between CD4+ and CD8+ T cells is based on the ability of CD4+ cells to recognize antigen presented in association with class II MHC molecules, and CD8+ cells to recognize antigen presented in association with class I MHC molecules. CD8+ cells are involved in "effector" functions in immune responses, such as direct cytotoxic destruction of target cells bearing foreign antigens, and represent an important mechanism for resistance to viral infections and tumors. The CD8+ cells that mediate this lytic function are designated cytotoxic T lymphocytes (CTLs). CD4+ T cells are generally involved in "helper" functions in immune responses and secrete cytokine molecules, in particular IL-2, upon which the cytotoxic CD8+ T cells are dependent. CD4+ T cells are often referred to as T helper (TH) cells. Although most CTL are of the CD8+ phenotype, some CTL of the CD4+ phenotype have been described. Generally, individual CTLs (whether CD8+ or CD4+) are antigen-specific.

Classes of lymphocytes, for example CTLs, are dependent on helper T (TH) cell-derived cytokines, such as IL-2, for growth and proliferation in response to foreign antigens. (Zinkernagel and Doherty, Adv. Immunol. 27:51, 1979; Male et al., Advanced Immunology, Chap. 7, Gower Publ., London, 1987; Jacobson et al., J. Immunol. 133:754, 1984). IL-2, for example, is a potent mitogen for cytotoxic T lymphocytes (Gillis and Smith, Nature 268:154, 1977), and the combination of antigen and IL-2 cause proliferation of primary CD8+ T cells in vitro. The importance of IL-2 for the growth and maintenance of the CD8+ CTL in vivo has been documented in models of adoptive immunotherapy in which the therapeutic efficacy of transferred anti-retroviral CD8+ cells is enhanced on subsequent administration of IL-2 (Cheever et al., J. Exp. Med. 155:968, 1982; Reddehase et al., J. Virol. 61:3102, 1987). IL-4 and IL-7 are also capable of stimulating the proliferation of mature CD8+ CTL (Alderson et al., J. Exp. Med. 172:577, 1990).

Considerable research has been focused on the use of T cells in treating malignant tumors and viral infections. Cytotoxic T cells specific for a particular type of tumor can be isolated and administered to a patient having a tumor, with the effect that the CTLs ameliorate the tumor. It has been demonstrated, for example, that tumor-specific T cells can not only be generated to experimental tumors in mice, but also that T cells with apparent tumor specificity can be isolated from human tumors. Such human tumor infiltrating lymphocytes (TILs) have been expanded in vitro and used to treat cancer patients, generating significant enthusiasm for human adoptive immunotherapy with tumor-specific T cells (Rosenberg et al., N. Engl. J. Med. 319:1767, 1988).

Similar studies using cytotoxic T cells specific for viral antigens have also been conducted in animal models. Human HIV-specific CTL of both the CD8+ (Walker et al., Nature 328:345, 1987; Plata et al., Nature 328:348, 1987) and CD4+ (Siliciano et al., Cell 54:561, 1988) phenotype have been isolated and characterized. HIV-specific CD8+ CTL are classical CTL in that their proliferative and cytotoxic responses are antigen-specific and MHC-restricted (Walker et al., supra; Chenciner et al., Eur. J. Immuno. 19:1537, 1989; Walker et al., Proc. Natl. Acad. Sci. USA 86:9514, 1989), in common with the numerous mouse and human CTL clones which have been characterized which are specific for viral, tumor or allospecific antigens.

The adoptive transfer of antigen (Ag)-specific T cells to establish immunity appears to be an effective therapy for some viral infections and tumors in the mouse animal model system. (For a review, See P. D. Greenberg, in Advances in Immunology F. Dixon Ed. Academic Press, Inc. Orlando Fla. (1991), pp. 280–355.) However, a successful outcome of an adoptive transfer method is dependent upon many factors, including the longevity of the transferred clones and the lack of toxicity to the host of the transferred cells. Although many antigen-specific T cell clones have been isolated, the use of tumor-specific T cell clones generated in vitro has been shown to have definite limitations in tumor therapy. It has been demonstrated in several therapeutic models that the efficacy of cytolytic CD8+ T cells is limited by a dependency on exogenous IL-2 (produced by TH cells), a finding that has been substantiated in human adoptive therapy trials in which administration of exogenous IL-2 appears essential for optimal therapeutic efficacy (Rosenberg et al., N. Engl. J. Med. 319:1767;, 1988; Klarnet et al., in Role of Interleukin-2 Activated Killer Cells in Cancer, Lutzova and Herberman (eds.), CRC Press, Florida, Chap. 14, pp. 199–218, 1990). Thus, while in vitro T cell cloning techniques provide a means to generate large numbers of T cells with demonstrable tumor or viral specificity, the full potential of using such antigen-specific T cells in therapy appears to be limited by their dependency on TH cells.

In some limited instances the problem of TH dependency may be circumvented by using a particular class of cells known to function independent of TH cells. These cells are known as helper-independent cytolytic CD8+ cells (HITc) (Klarnet et al., J. Immunol. 142:2187, 1989) and have been identified in populations of primary (i.e., freshly isolated from in vivo sources) CD8+ CTL (Sprent and Schaefer, J. Exp. Med. 162:21068, 1985; Andrus et al., J. Exp. Med. 159:647, 1984). HITc cells produce sufficient IL-2 to grow independently of CD4+ cells and the cytokines they produce. HITc cells are also known to express plasma membrane IL-1 receptors (IL-1R) and require IL-1 for their IL-2-independent proliferation (Klarnet et al., 1989, supra). This is in contrast to conventional CD8+ CTL which do not express detectable IL-1R on their surface (Lowenthal and MacDonald, 1987). HITc cells have been generated which are specific for a range of antigens, including tumor, viral and alloantigens (von Boehmer et al., 1. Immunol. 133:59, 1984; Klarnet et al., J. Immunol. 138:4012, 1987; and Andrus et al., J. Exp. Med. 149:647, 1984; Mizouchi et al., J. Immunol. 142:270, 1989). HITc specific for a retrovirally transformed tumor have been shown to eradicate the tumor cells and persist long-term in vivo following their engraftment (Klarnet et al., 1989, supra). Unfortunately, HITc cells having specificity for many important antigens, such as HIV antigens or tumor antigens, have not yet been isolated.

In order to realize the full potential of antigen-specific T cells in therapy, it is necessary to develop a more complete repertoire of CTLs that have a lessened dependency on TH cells. One approach has been the introduction of a recombinant vector that expresses a cytokine receptor, for example the IL-1 receptor, into TH-dependent CTL, resulting in the conversion to cells with a lessened requirement for the TH cells and/or their stimulatory factors. (PCT/US91/06921, WO 92/05794, published Apr. 16, 1992). The present invention, described below, presents a different approach to the production of lymphocytes with a lessened dependency on TH cells and/or the stimulatory factors they produce.

SUMMARY OF THE INVENTION

The present invention provides vectors for producing lymphocytes that are, relative to the parental cells without the vector, capable of enhanced growth or proliferation in the presence of limiting amounts of TH cells or stimulatory factors (e.g. cytokines) provided by TH accessory cells.

The vectors contain a recombinant gene, from which the expression of a desired gene product capable of enhancing growth or proliferation is controlled, at least in part, by a heterologous transcriptional control region. The transcriptional control region is from a gene that is responsive to lymphocyte activation by the presence of a cognate antigen associated with the MHC of the target cell. Thus, the invention provides the benefit of regulating expression of the stimulatory factor(s) so that they are coordinated with antigen activation of the lymphocyte.

The invention also provides lymphocytes containing the vectors, and methods of using the vectors to create lymphocytes with a lessened dependency on TH cells and/or stimulatory factors they produce.

Thus, one embodiment of the invention is a recombinant polynucleotide comprised of a region encoding a stimulatory factor polypeptide operably linked to a heterologous transcriptional control region, wherein expression of the stimulatory factor polypeptide in an activated lymphocyte reduces the dependency on lymphocyte T helper cells (TH cells), and wherein when the lymphocyte is activated by its cognate antigen, the transcriptional control region causes transcription of the stimulatory factor encoding region.

Another embodiment of the invention is a host cell and progeny thereof, wherein the host cell is transformed with a recombinant polynucleotide comprised of a region encoding a stimulatory factor polypeptide operably linked to a heterologous transcriptional control region, wherein expression of the stimulatory factor polypeptide in an activated lymphocyte reduces the dependency on lymphocyte T helper cells (TH cells), and wherein when the lymphocyte is activated by its cognate antigen, the transcriptional control region causes transcription of the stimulatory factor encoding region.

Yet another embodiment of the invention is a method of using the above described polynucleotide comprising transforming a lymphocyte with the polynucleotide, wherein as a result of the transformation the lymphocyte is rendered of lessened dependency on TH cells for proliferation.

Another embodiment of the invention is a cell produced by the above-described method, and progeny thereof.

DETAILED DESCRIPTION OF THE INVENTION

Figure 1:
FIG. 1 presents schematic illustrations of the proviral structures of the retroviral vectors named HyTK/hIL-3/CAT and HyTK/hIL-4/CAT.
Figure 1:
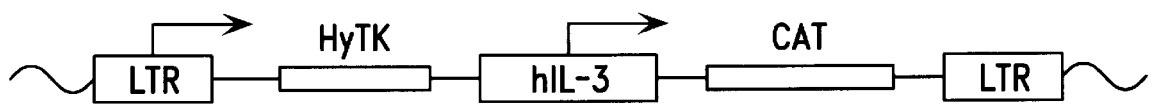

The invention provides antigen specific lymphocytes that differ from the parental TH-dependent lymphocytes by virtue of the presence of a recombinant polynucleotide that encodes at least one polypeptide that stimulates the proliferation of the lymphocytes, expression of which is usually de minimis in the parental TH-dependent lymphocytes. The encoding sequence is operably linked to a transcriptional control region which is heterologous to it. The transcriptional control region is from a gene that is responsive to lymphocyte activation by the presence of a cognate antigen associated with the MHC of the target cell. Thus, antigen activation of the lymphocytes also signals transcription of the encoded polypeptide sequence. The cells containing the recombinant polynucleotide are preferably CD8+ CTLs.

"Lymphocytes" as used herein, are cells that specifically recognize and respond to non-self or self antigens, and are responsible for development of specific immunity. Included within "lymphocytes" are B-lymphocytes and T-lymphocytes of various types.

"Cytotoxic T lymphocytes" or "CTLs" are T cells which bear the CD3 cell surface determinant and mediate the lysis of target cells bearing cognate antigens. CTLs may be of either the CD8+ or CD4+ phenotype. CTLs are generally antigen-specific and MHC-restricted in that they recognize antigenic peptides only in association with the Major Histocompatibility Complex (MHC) molecules on the surface of target cells. CTLs may be specific for a wide range of viral, tumor or allospecific antigens, including HIV, EBV, CMV and a wide range of tumor antigens. Some CTLs, however, may not be antigen specific. For example, some cloned CTLs can be induced to lose some of their specificity for their cognate antigen by culture in abnormally high concentrations of IL-2 (Brooks et al., Immunol. Rev. 72:43, 1983).

A "TH-independent" CTL or lymphocyte or a "lymphocyte with lessened dependence on a TH cell" is one that relative to parental lymphocytes from which the subject lymphocyte was derived is capable of enhanced growth or proliferation in the presence of limiting quantities of CD4+ T helper (TH) cells and/or one or more derived TH cell cytokines or their equivalents. Growth or proliferation may be measured, for example, by any in vitro proliferation or growth assay or by any assay measuring the ability of the CTL to persist in vivo. Specific examples of suitable assays are known in the art. CTLs capable of enhanced growth or viability may have augmented ability to destroy target cells bearing the foreign antigens or provide long-term immunologic memory.

As used herein, "stimulatory factor" or "growth factor" or "stimulatory polypeptide" or "stimulatory polypeptide factor" refers to a polypeptide that stimulates cell proliferation, including lymphocyte proliferation. Included within the term are, for example, cytokines, stimulatory polypeptide transcription factors, receptors (including modified and recombinant and hybrid forms), oncogenes, and other hormones that are not cytokines (e.g., growth hormone, prolactin and IGF-1).

"Cytokine" refers to a polypeptide that is a soluble intercellular signalling molecule, including for example, the interleukins, interferons, colony stimulating factors and TNFs.

The term "polypeptide" refers to a polymer of amino acids and does not refer to a specific length of the product; thus, peptides, oligopeptides, and proteins are included within the definition of polypeptide. This term also does not refer to or exclude post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

"Treatment" as used herein refers to prophylaxis and/or therapy. "Helper T cells" or "Helper cells" or "TH cells" are a functional subclass of T cells which can help to generate cytotoxic T cells and cooperate with B cells in the production of an antibody response. Helper cells usually recognize antigen in association with class II MHC molecules.

An "antigen specific T cell clone" is comprised of the progeny of a single cell; the cells in this type of clone are of the same phenotype and are all targeted towards the same antigen. Methods of preparing antigen-specific T cell clones are known in the art.

The term "recombinant expression vector" refers to a replicable unit of DNA or RNA in a form which is capable of being introduced into a target cell by transformation, electroporation, transduction or viral infection, and which codes for the expression of a heterologous structural coding sequence, for example, a cytokine, which is transcribed into mRNA and translated into protein under the control of elements having a regulatory role in gene expression. Such vectors will preferably also contain appropriate transcription and translation control sequences, including initiation sequences operably linked to the coding sequence.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence, for example cytokines, can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions. Thus, the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. "Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A CTL is "cytolytically specific for" cells expressing tumor or viral antigens if the CTL is capable of selectively recognizing and lysing the cells bearing the tumor or viral antigen. A CTL is "cytolytically reactive against" cells expressing tumor or viral antigens if the CTL is capable of lysing the cells bearing the tumor or viral antigen, without regard to its ability to selectively recognize such cells. "Activation-induced expression" refers to expression that occurs when the T cell is stimulated by any of a number of methods known in the art including, but not limited to, stimulation by cognate antigen, stimulation by cross-linking the T cell receptor with anti-CD3 antibody, and stimulation with chemical agents such as a combination of phorbol myristic acid ("PMA") and ionomycin.

"Antigen-induced expression" or "antigen-specific expression" refers to expression that occurs when the T cell recognizes its cognate antigen. "Cognate antigen" refers to an antigen, a peptide of which when associated with an MHC molecule forms a ligand that binds to a lymphocyte that recognizes it and causes triggering of signals for the effector function of the cell and/or for proliferation.

An "activated lymphocyte" is one that as a result of stimulation by any of a number of methods known in the art including, but not limited to, stimulation by cognate antigen, stimulation by cross-linking the T cell receptor with anti-CD3 antibody, and stimulation with chemical agents such as a combination of phorbol myristic acid ("PMA") and ionomycin, is expressing gene products (including, for example, cytokines) at a level that is elevated relative to a lymphocyte that has not been so activated.

A "transcriptional control region" (sometimes referred to as a "transcriptional regulatory region") encompasses all the elements necessary for transcription, and may include elements necessary for regulation and cell-specific transcription. Thus, a transcriptional control region includes at least the promoter sequence, and may also include other regulatory sequences such as enhancers, and transcription factor binding sites.

A "transcriptional control region heterologous to a coding region" is one that is not normally associated with the coding region in nature.

"Operably linked" refers to a juxtaposition wherein the components so described are in a relationship permitting them to function in their intended manner. For instance, a promoter is operably linked to a coding sequence if the promoter affects its transcription or expression.

"Regulatory Sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

An "individual" as used herein refers to vertebrates, particularly members of the mammalian species, and includes but is not limited to domestic animals, sports animals, and primates, including humans.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos Eds. 1987), HANDBOOK OF EXPERIMENTAL IMMUNOLOGY, (D. M. Weir and C. C. Blackwell, Eds.); CURRENT PROTOCOLS IN MOLECULAR BIOLOGY, (F. M. Ausubel, R. Brent, R. E. Kingston, D. D. Moore, J. G. Siedman, J. A. Smith, and K. Struhl Eds. 1987); and CURRENT PROTOCOLS IN IMMUNOLOGY (J. E. Coligan, A. M. Kruisbeek, D. H. Margulies, E. M. Shevach and W. Strober Eds. 1991). All patents, patent applications, and publications mentioned herein, both supra and infra, are hereby incorporated herein by reference.

TH-independent CTLs are created from TH-dependent CTLs by the insertion of a recombinant polynucleotide containing a sequence encoding at least one stimulatory factor operably linked to a heterologous coding sequence. The stimulatory factor is one that stimulates or enhances proliferation of CTLs, particularly antigen-activated CTLs. In preferred embodiments the stimulatory factor is a cytokine, including, for example, members of the family of interleukins (ILs), interferons (IFNs), TGF-β, tumor necrosis factors (TNFs), colony stimulating factors (CSFs), and growth factors (GFs). A number of cytokine encoding sequences have been isolated and sequenced. (See, for example, Annual Reviews in Biochemistry 59:783–836 (1990) for a review of cytokines). In a preferred embodiment the cells converted to TH-independence are CD8+ cells, and the stimulatory factor is preferentially IL-2. Methods of determining the effect of stimulatory factors on the proliferation of CTLs are known within the art.

The transcriptional control region to which the region encoding the stimulatory factor is operably linked is one which is regulatable, and that functions in T cells, and preferably in CD8+ CTLs. Preferably, the transcriptional control region is responsive to activation of the T lymphocyte, particularly the CD8+ CTLs, by its cognate antigen. This causes activation of the transcriptional control region and expression of the stimulatory factor gene under conditions when it is desirable to stimulate proliferation of the activated CTLs.

Transcriptional control regions are known in the art, and include, for example, regions isolated from the following: the human cytomegalovirus (HCMV) IE94 gene (M. Boshart et al. (1985), Cell 41:521–530); the human IL-2 gene (T. Fujita et al. (1986), Cell 46:401–407); the human IFN-γ gene (V. C. Ciccarone et al. (1990), J. Immunol. 144:725–730); the human IL-3 gene (S. G. Shoemaker et al. (1990), Proc. Natl. Acad. Sci. USA 87:9650–9654); the human IL4 gene (N. Arai et al. (1989), J. Immunol. 142:274–282; the human lymphotoxin gene (G. E. Nedwin, S. L. Naylor, A. Y. Sakaguchi, D. Smith, J. Jarrett-Nedwin, D. Pennica, D. V. Goeddel, and P. W. Gray (1985), Nucl. Acids. Res. 13:6361–6373); the human granulocyte-macrophage CSF (GM-CSF) gene (S. Miyatake et al. (1985), EMBO J. 4:2561–2568; the human perforin gene (M. G. Lictenheld et al. (1989), J. Immunol. 143:4267–4274); the human 519 gene (W. C. Manning et al. (1992), J. Immunol. 148:40364042); the human granzyme B (CTLA-1) gene (P. Haddad et al. (1990), Gene 87:265–271; the human CTLA-4 gene (K. Harper et al. (1991), J. Immunol. 147:1397–1044); the human CGL-2 gene (J. W. Heusel et al. (1991), J. Biol. Chem. 266:6152–6158); the human granzyme H gene (P. Haddad et al. (1990), Int. Immunol. 3:57–66; the human IL-2 receptor, α chain gene (S. L. Cross et al. (1987), Cell 49:47–56); the murine T cell activation 3 (TCA-3) gene (S. D. Wilson et al. (1988), J. Immunol. 141:1563–1570); the murine CD69 gene (F. Ziegler et al. (1994), J. Immunol. 152:1228–1236); and the human CD69 gene.

Amongst the transcriptional control regions, those that are predominantly active in activated CD4+ helper T cells (TH cells) are those from the IL-2 and IL-4 genes. Those predominantly active in activated CD8+ CTLs are from the following genes: lymphotoxin, perforin, 519, Granzyme H, CTLA-1, and CGL-2. Of particular interest are those active in both activated CD4+ TH cells and CD8+ CTLs, including inter alia, transcriptional control regions from the following genes: IFN-γ, IL-3, GM-CSF, CTLA-4, the IL-2 receptor α chain, TCA-3, and CD9.

In some embodiments of the invention, the transcriptional control regions are hybrids. For example, enhancer regions (e.g., from the HCMV IE transcriptional control region and/or from the SV40 early transcriptional control region) may be inserted upstream of, downstream of, or into the transcriptional control regions. Alternatively or in addition, multimeric transcription factor binding sites (e.g. NF-AT and/or NF-KB) may be inserted upstream of, downstream of, or into the transcriptional control regions (see, e.g., C. L. Verweij et al. (1990) J. Biol. Chem. 265:15788–15795 (describing NF-AT); and K. Briegel et al. (1991) Nucl. Acids Res. 19:5929–5936 (describing NF-KB). The upstream region of one transcriptional control region may also be combined with the proximal region of another.

It is contemplated that overexpression of a stimulatory factor (for example, a lymphokine or a cytokine) or infusion of large numbers of antigen-specific CTL may be toxic to the treated individual. Therefore, it is within the scope of the invention to include gene segments that cause the T cell clones of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes (also referred to as "negative selectable markers" or "suicide genes") are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphoribosyltransferase (HPRT) gene, the cellular adenine phosphoribosyltransferase (APRT) gene, and bacterial cytosine deaminase (Mullen et al., Proc. Natl. Acad. Sci. USA. 89:33 (1992)).

In addition, it is useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Preferably, the positive selectable marker and the negative selectable element are linked such that gain or loss of the negative selectable element necessarily also is accompanied by gain or loss of the positive selectable marker. Even more preferably, the positive and negative selectable markers are fused so that gain or loss of one obligatorily leads to gain or loss of the other. An example of a fused polynucleotide that yields as an expression product a polypeptide that confers both the desired positive and negative selection features described above is a hygromycin phosphotransferase-thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374–3378, 1991. See, also, the description of Bifunctional Selectable Fusion Genes by Lupton, S. D., WO 92/08796 (international publication date 29 May 1992).

Techniques for nucleic acid manipulation are described generally, for example, in Sambrook et al. (1989), supra., Ausubel et al., (1987), supra and in Annual Reviews of Biochemistry (1992) 61:131–156. Reagents useful in applying such techniques, such as restriction enzymes and the like, are widely known in the art and commercially available from a number of vendors.

Large amounts of the polynucleotides used to create the cells of the present invention may be produced by replication in a suitable host cell. The natural or synthetic polynucleotide fragments coding for a desired fragment may be incorporated into recombinant nucleic acid constructs, typically polynucleotide constructs, capable of introduction into and replication in a prokaryotic or eukaryotic cell. Usually the constructs will be suitable for replication in a unicellular host, such as yeast or bacteria, but may also be intended for introduction to, with or without integration within the genome, cultured mammalian or plant or other eukaryotic cell lines. The purification of nucleic acids produced by the methods of the present invention are described, e.g., in Sambrook et al. (1989).

The polynucleotides used in the present invention may also be produced in part or in total by chemical synthesis, e.g., by the phosphoramidite method described by Beaucage and Carruthers (1981) Tetra. Letts. 22:1859–1862 or the triester method according to Matteucci et al. (1981) J. Am. Chem. Soc. 10:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host cell for replication will typically comprise a replication system recognized by the host, including the intended recombinant polynucleotide fragment encoding the desired polypeptide. Such vectors may be prepared by means of standard recombinant techniques well known in the art and discussed, for example, in Sambrook et al. (1989) or Ausubel et al (1987).

Preferably, during the cloning phase, the polynucleotide construct will contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker will depend on the host cell, and appropriate markers for different hosts are well known in the art.

The polynucleotides conferring T$_H$-independence upon CTLs may be introduced into the desired type Ag-specific T cell by means known in the art, including, for example, transformation, electroporation, lipofection, and transduction, including the use of adeno-associated viral (AAV) vectors, and particularly using methods of retroviral gene transfer known in the art.

Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., Proc. Natl. Acad. Sci. USA 84 82:158, 1985), adenoviruses (Karlsson et al., EMBO J. 5:2377, 1986), adeno-associated virus (AAV) (B. J. Carter, Current Opinion in Biotechnology 1992, 3:533–539), and retroviruses (Coffin, 1985, pp. 17–71 in Weiss et al. (eds.), RNA Tumor Viruses, 2nd ed., Vol. 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., Oncogene 3:123, 1988), and infection with recombinant adenovirus (Karlsson et al., supra; Reuther et al., Mol. Cell. Biol. 6:123, 1986), adeno-associated virus (LaFace et al., supra) and retrovirus vectors (Overell et al., Oncogene 4:1425, 1989). Primary T lymphocytes have been successfully transduced by electroporation (Cann et al., supra, 1988) and by retroviral infection (Nishihara et al., Cancer Res. 48:4730, 1988; Kasid et al., supra, 1990).

Retroviral vectors provide a highly efficient method for gene transfer into eukaryotic cells and are the preferred method for the delivery of the polynucleotides of the invention into the T$_H$-dependent CTLS. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acing sequences necessary for viral replication.

A "provirus" refers to the DNA reverse transcript of a retrovirus which is stably integrated into chromosomal DNA in a suitable host cell, or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (Cell 33:153, 1983) describe the development of cell lines (e.g., ψ2) which can be used to produce helper-free stocks of recombinant retrovirus. These cell lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring trans-acting elements encoding an ecotropic viral envelope (e.g., ψ2) provides ecotropic (limited host range) progeny virus. Alternatively, assembly in a cell line containing amphotropic packaging genes (e.g., PA317, ATCC CRL 9078; Miller and Buttimore, Mol. Cell. Biol. 6:2895, 1986) provides amphotropic (broad host range) progeny virus. Such packaging cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds. ), RNA Tumor Viruses, 2nd ed., vol. 2 (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., Mol. Cell. Biol. 8:1803, 1983).

Retroviral vectors have been used as genetic tags by several groups to follow the development of murine hematopoietic stem cells which have been transduced in vitro with retrovirus vectors and transplanted into recipient mice (Williams et al., Nature 310:476, 1984; Dick et al., Cell 42:71, 1985; Keller et al., Nature 318:149, 1985). These studies have demonstrated that the infected hematopoietic cells reconstitute the hematopoietic and lymphoid tissue of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (N. Engl. J. Med. 323:570, 1990). The transduction of these cells with the marker gene was not associated with in vitro cellular dysfunction (Kasid et al., Proc. Natl. Acad. Sci. USA 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of co-expressing a dominant selectable marker gene in the vector, thus allowing selection of cells which are expressing specific vector sequences.

The lymphocyte clones of the invention, i.e., those that are of lessened dependency on one or more stimulatory factors produced by $T_H$ cells, may be used to confer immunity to individuals. By "immunity" is meant a lessening of one or more physical symptoms associated with a response to infection by the pathogen, and/or symptoms associated with malignancy, to which the T cell is directed. The amount of cells administered is usually in the range present in normal individuals with immunity to the pathogen and/or malignancy. Thus, CD8+ CD4-cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician or veterinarian, and can be determined by routine examination.

The following publications, referred to in Examples 10–27, are hereby incorporated by reference in their entirety:

J. M. Allen, K. A. Forbush and R. M. Perlmutter (1992) Functional dissection of the lck proximal promoter. Mol. Cell. Biol. 12:2758–2768.

N. Arai, D. Nomura, D. Villaret, R. DeWaal Malefijt, M. Seiki, M. Yoshida, S. Minoshima, R. Fukuyama, M. Maekawa, J. Kudoh, N. Shimuzu, K. Yokata, E. Abe, T. Yokata, Y. Takebe, and K. Arai (1989) Complete nucleotide sequence of the chromosomal gene for human IL-4 and its expression. J. Immunol. 142:274–282.

F. M. Ausubel, R. Brent, R. E. Kingston, D. D. Moore, J. G. Siedman, J. A. Smith, and K. Struhl Eds. (1987) Current protocols in molecular biology. Wiley, New York.

M. Boshart, F. Weber, G. Jahn, K. Dorsch-Häsler, B. Fleckenstein, and W. Schaffner (1985) A very strong enhancer is located upstream of an immediate early gene of human cytomegalovirus. Cell 41:521–530.

V. C. Ciccarone, J. Chrivia, K. J. Hardy, and H. A. Young (1990) Identification of enhancer-like elements in human IFN-γ genomic DNA. J. Immunol. 144:725–730.

S. L. Cross, M. B. Feinberg, J. V. Wolf, N. J. Holbrook, F. Wong-Staal and W. J. Leonard (1987) Regulation of the human interleukin-2 receptor α chain promoter: Activation of a nonfunctional promoter by the transactivator gene of HTLV-1. Cell 49:47–56.

P. W. Gray and D. V. Goeddel (1982) Structure of the human immune interferon gene. Nature 298:859–863.

J. W. Heusel, R. D. Hanson, G. A. Silverman and T. J. Ley (1991) Structure and expression of a cluster of human hematopoietic serine protease genes found in chromosome 14q11.2. J. Biol. Chem. 266:6152–6158.

S. D. Lupton, L. L. Brunton, V. A. Kalberg and R. W. Overell (1991) Dominant positive and negative selection using a hygromycin phosphotransferase-Thymidine kinase fusion gene. Mol. Cell. Biol. 11:3374–3378.

R. Mann, R. C. Mulligan and D. Baltimore (1983) Construction of a retrovirus packaging mutant and its use to produce helper-free retrovirus. Cell 33:153–159.

A. D. Miller and C. Buttimore (1986) Redesign of retrovirus packaging cell lines to avoid recombination leading to helper virus production. Mol. Cell. Biol. 6:2895–2902.

G. E. Nedwin, S. L. Naylor, A. Y. Sakaguchi, D. Smith, J. Jarrett-Nedwin, D. Pennica, D. V. Goeddel, and P. W. Gray (1985) Human lymphotoxin and tumor necrosis factor genes: Structure, homology and chromosomal localization. Nucl. Acids Res. 17:6361–6373.

S. R. Riddell and P. D. Greenberg (1990) The use of anti-CD3 and anti-CD28 monoclonal antibodies to clone and expand human antigen-specific T cells. J. Immunol Methods 128:189–201.

S. R. Riddell, M. Rabin, A. P. Geballe, W. J. Britt, and P. D. Greenberg (1991) Class I MHC-restricted cytotoxic T lymphocyte recognition of cells infected with human cytomegalovirus does not endogenous viral gene expression. J. Immunol. 146:2795–2804.

S. G. Shoemaker, R. Hromas, and K. Kaushansky (1990) Transcriptional regulation of interleukin 3 gene expression in T lymphocytes. Proc. Natl. Acad. Sci. USA 87:9650–9654.

The examples presented below are provided as a further guide to the practitioner of ordinary skill in the art, and are not to be construed as limiting the invention in any way.

EXAMPLE 1

Preparation of CD3+, CD8+, CD4-CMV-specific T Cell Clones

The cells are prepared essentially as described in S. R. Riddell, M. Rabin, A. P. Geballe, W. J. Britt, and P. D. Greenberg, 1. Immunol. 146, 2795 (1991). More specifically, for isolation of CD3+, CD8+, CD4-CMV-specific T cell clones, autologous fibroblasts are infected with AD169 strain CMV for 6 hours and then cultured for 7 days with autologous PBL in RPMI 1640 medium (JRH Biosciences) supplemented with 25 mM HEPES, 11% human CMV seronegative AB serum, 4mM L-glutamine and 25 μM 2-ME. Cultures are restimulated with autologous CMV-infected fibroblasts and gamma-irradiated (3300 rads) PBL as feeder cells and supplemented 2 days later with 2–5 U/ml IL-2. Seven days following restimulation, CD8+ T cells are enriched and plated in 96 well round bottom wells at 0.3–0.8 cells/well with autologous gamma irradiated feeder cells, autologous CMV-infected fibroblasts, and 50 U/ml IL-2. Wells positive for growth are evident in 10–14 days. Clones which demonstrate class I MHC restricted CMV-specific cytolytic reactivity are confirmed by indirect immunofluorescence to be CD3+ CD8+ and CD4−. These clones are propagated to large numbers in 12 well plates or 75 cm² tissue culture flasks by restimulation every 7–10 days with autologous CMV-infected fibroblasts and gamma-irradiated feeder cells, and the addition of 25–75 U/ml IL-2 at 2 and 4 days following restimulation.

EXAMPLE 2

Generation of CD8+ HIV gag-Specific T cell Clones

Peripheral blood mononuclear cells (PBL) are obtained from an HIV seropositive bone marrow transplant recipient by venipuncture for a volume of 60 cc followed by Ficoll Hypaque density gradient centrifugation. The PBL are washed twice in sterile phosphate buffered saline, suspended in culture media consisting of RPMI 1640 medium, 25 mM Hepes, and 4mM L glutamine and then placed in sterile tissue culture dishes for separation into adherent and non-adherent populations by culture for two hours at 37° C. The adherent cells are infected with a vaccinia HIV gag recombinant virus (vac/gag) at a multiplicity of infection of 5, in RPMI 1640 medium, 25 mM Hepes, 10% human AB serum, and 4 mM L glutamine. After a twelve to fourteen hour incubation, the vac/gag infected adherent cells are UV irradiated under a germicidal lamp to inactivate vaccinia, and then gamma irradiated (3000 rads) prior to use as stimulators. The separated non-adherent cells are cultured overnight at 37° C. in RPMI 1640 medium, 25 mM Hepes, 10% human AB serum, and 4 mM L glutamine, and added to the UV inactivated, gamma irradiated vac/gag infected adherent cells at a responder to stimulator ratio of 30 to 1. Cultures are incubated at 37° C. in 5.5% $CO_2$ in a Forma Stericult incubator.

Seven days later, cultures are restimulated with donor-derived UV inactivated, gamma irradiated vac/gag infected adherent cells and supplemented with gamma irradiated (3000 rads) donor PBL as feeder cells. Cultures are fed 48 to 96 hours after restimulation with recombinant IL-2 (2 to 5 U/ml) and incubated for seven days after restimulation.

These cell lines are tested in a chromium release assay for lytic activity against donor-derived and HLA mismatched vac/gag, vac, and mock infected fibroblasts prior to T cell cloning to confirm the presence of Class I MHC-restricted gag-specific cytolytic activity.

To clone CD8+ HIV gag-specific $T_c$, the cell lines are depleted of CD4+ T cells using the monoclonal antibody, OKT4 (Ortho) plus rabbit complement, and the enriched CD8+ T cells plated at limiting dilution in 96 well round bottomed plates. Each well receives $1.5 \times 10^3$ UV inactivated and gamma irradiated vac/gag-infected donor-derived adherent cells or EBV LCL as stimulators, $5-10^4$ gamma irradiated (3000 rads) donor-derived PBL and $1 \times 10^4$ gamma irradiated (8000 rads) donor-derived LCL as feeder cells in 0.2 ml of culture media containing 25 to 50 units IL-2 per ml.

Wells positive for growth are identified 10 to 14 days after plating and are screened in a microcytotoxicity assay to identify those clones with Class I MHC-restricted cytolytic activity for HIV gag expressing target cells. Positive clones are transferred to 24 well plates and restimulated with UV inactivated and gamma irradiated vac/gag-infected LCL, with irradiated donor-derived PBL added as feeder cells. The cultures are fed with IL-2 50 U/ml 48 to 96 hours after restimulation. T cell clones are restimulated every seven days and transferred to six well plates and 75 cm² flasks for expansion. All clones are retested for Class I MHC restricted gag-specific cytolytic activity, and cell surface phenotype (CD3, CD4, CD8 and CD16). T cell clones demonstrating rapid in vitro growth, Class I MHC restricted gag-specific cytolytic activity, and a CD3+, CD8+, CD4−, CD16− phenotype are selected for infection with the HyTK retrovirus containing a stimulatory factor gene under the control of an antigen-regulated transcriptional control region.

EXAMPLE 3
Transduction and Selection of human CD8+ HIV gag-specific $T_c$ clones with retroviral vectors HIV gag-specific CD8+ $T_c$ clones generated as described above are stimulated with UV inactivated, gamma irradiated vac/gag-infected LCL. Twenty-four hours later, 50 U/ml or IL-2 are added to induce T cell proliferation. Twenty-four hours later, the cells are harvested, pelleted and suspended at 1×10 cells in 1 ml of RPMI 1640 medium, 25 mM Hepes, 10% human AB serum, and 4 mM L glutamine with 100 U/ml of IL-2. One ml of retroviral supernatant is added with polybrene (5 μg/ml) and the cells incubated at 37° C. in 5.5% $CO_2$ for 48 hours. The T cell clones are then pelleted and resuspended in fresh media with 25 U/ml of IL-2. Following a four-day incubation, T cells are subcloned by limiting dilution in 96 well round bottom plates. At this time, anti-CD3 monoclonal antibody is used in the cloning cultures to stimulate T cell growth, using essentially procedures described in Riddell, S R and Greenberg P D, J. Immunol. Methods 128:189 (1990). irradiated donor derived PBL ($5×10^4$/well), and LCL ($1×10^4$/well) are used as feeder cells and all wells receive 50 U/ml of recombinant IL-2. At seven days, all wells are fed with hygromycin B to a final concentration of 300 μg/ml). At day 14 growing clones are restimulated with anti-CD3 monoclonal antibody in the presence of donor-derived PBL and LCL as accessory cells. Clones are fed with 50 U/ml recombinant IL-2 48 to 96 hours after stimulation and are restimulated every seven days. The appropriate selective drug at its active concentration is added to the cultures 48 hours after stimulation and maintained until the next restimulation.

EXAMPLE 4
Regulated Expression in T cells of a Reporter Gene Controlled by Transcriptional Regulator Regions from Lymphokine Genes (Activation-induced expression mediated by the IL-3 and IL4 transcriptional control regions in human Jurkat T lymphocytes)

Plasmid DNAs containing transcriptional control regions from human IL-3 (hIL-3) or human IL-4 (hIL-4) genes operably linked to a reporter gene encoding chloramphenicol acetyl transferase (CAT) were prepared in HyTK containing vectors. The following is for construction of HyTK/hIL-3/CAT and HyTK/hIL-4/CAT. HyTK/hIL-3/CAT was constructed using standard techniques (Ausubel et al., 1987) as follows: The human IL-3 promoter was amplified directly from human genomic DNA by PCR using oligonucleotides 5'-CACACACAAGCTTGCCACCCACCAGGACCAAG CAGGGCGGGC-3' (SEQ ID NO:1) and 5'-ACACACACG GATCCGCAGGAGGCACTCTGTCTTGTTCTG-3' (SEQ ID NO:2). The PCR product was digested with HindIII and BamHI, and ligated into a derivative of tgLS(+)HyTK (Lupton et al. 1991) containing a CAT gene, and unique HindIII and BamHI sites 5' to the CAT gene. HyTK/hIL-4/CAT was constructed using standard techniques (Ausubel et al., 1987) as follows: The human IL4 promoter was amplified directly from human genomic DNA by PCR using oligonucleotides 5'-CACACACAAGCTTCAATAAAAAA CAAGCAGGGCGCGTGGT-3' (SEQ ID NO:3) and 5'-A CACACACGGATCCATTTGCAGTGACAATGTGAG GCAATTAGT-3' (SEQ ID NO:4). The PCR product was digested with HindIII and BamHI, and ligated into a derivative of tgLS(+)HyTK (Lupton et al., 1991) containing a CAT gene, and unique HindIII and BamHI sites 5' to the CAT gene.

The resulting vectors, named HyTK/hIL-3/CAT and HyTK/hIL-4/CAT have structures as schematically shown in FIG. 1. In the figure "LTR" signifies the long terminal repeat segments of the retroviral vector, and HyTK signifies the hygromycin phosphotransferase-thymidine kinase fusion gene that is operably linked to the LTR transcriptional control region. hIL-4 and hIL-3 are the transcriptional control regions from hIL-4 and hIL-3, respectively, operably linked to the CAT gene. The arrows show the direction of transcription from the transcriptional control regions.

The plasmid DNAs (50 μg each) were electroporated into separate preparations of Jurkat cells ($4×10^8$ cells) in 0.8 ml of complete medium using a 0.4 cm cuvette and a Biorad Gene Pulser set at 300 V and 960 μF. Jurkat cells were grown in RPMI 1640 medium supplemented with 10% fetal bovine serum, 0.1 mM non-essential amino acids, 50 μM 2-mercaptoethanol, 2 mM L-glutamine, 50 U/ml penicillin, and 50 μg/ml streptomycin at 37° C. in a humidified atmosphere supplemented with 5% $CO_2$. Following electroporation, the cells were returned to culture and either left unstimulated (−), or were stimulated with 10 ng/ml of phorbol myristic acid (PMA) and 500 ng/ml of ionomycin (+). After 72 h in culture, the cells were harvested, and extracts were prepared and assayed for CAT activity using standard techniques (Ausubel et al., 1987) as follows: The transfected cells were harvested by centrifugation, resuspended in 100 μl of 0.25M Tris (pH 8.0), and subjected to 3 cycles of freezing (−20° C. for 5 min) and thawing (37° C. for 5 min). Cell debris was pelleted by centrifugation, and the supernatant was transferred to a clean tube. A 50 μl aliquot of extract was mixed with 78 μl of 0.5M Tris (pH 8.0), 20 μl of 24 mM acetyl coenzyme A, and 2 μl of [$^{14}$C]-labelled chloramphenicol, and the mixture incubated at 37° C. for 20–24 h. The reaction was extracted with 1 ml of ethyl acetate, the ethyl acetate extract was evaporated to dryness, and resuspended in 30 μl of ethyl acetate. The extract was then applied to a thin layer chromatogram, which was developed in a mixture of 95% chloroform/5% methanol. The chromatogram was then exposed to X ray film, or visualized using a phosphorimager.

Figure 2:
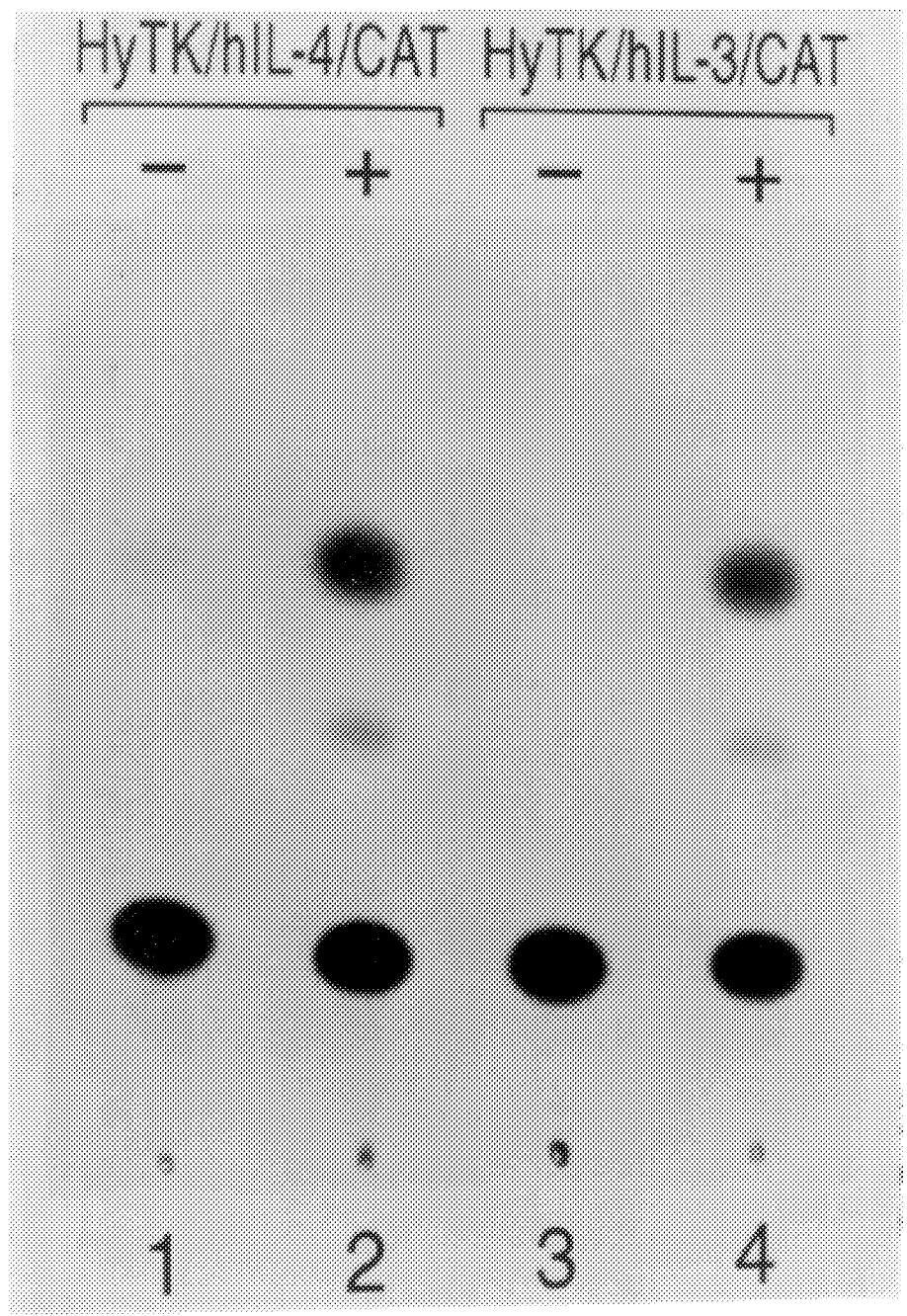
FIG. 2 is a half tone reproduction of the results of an assay for CAT activity from expression in non-stimulated and stimulated Jurkat cells transfected with the vectors HyTK/hIL-3/CAT or HyTK/hIL-4/CAT.

The results of the CAT assays, shown in FIG. 2, demonstrate that the hIL-4 and hIL-3 transcriptional control regions confer expression in human T lymphocytes, and that the level of expression of the reporter gene is increased upon T cell activation. The results further demonstrate that the hIL-4 and hIL-3 transcriptional control regions are functional when inserted into a retroviral vector.

EXAMPLE 5
Preparation of TH-Independent CD8+ CTL

Retroviral vectors are generated using plasmids are prepared as in Example 4, except that the coding sequence for CAT is replaced by the coding sequence for hIL-2. These vectors are inserted into CMV-specific and HIV-specific CD8+ CTLs as prepared in Examples 1 and 2. The transduced CTLs and control CTLs are monitored for proliferation in the absence of TH cells and in the presence and absence of the amount of IL-2 required for proliferation of the control CTLs. Proliferation of transduced CTLs but not control CTLs in the limiting amounts of added IL-2 is indicative of a lessened dependence on TH cell stimulatory factor, i.e., IL-2.

Figure 3:
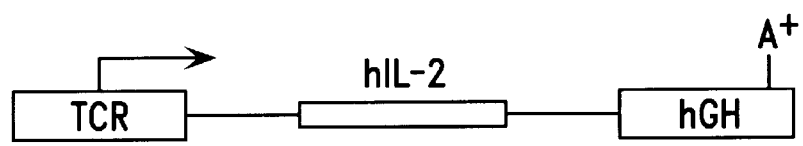
FIG. 3 presents a schematic illustration of nonviral vectors containing a heterologous transcriptional control region operably linked to a cytokine coding sequence.

EXAMPLE 6
Structure of Non-Viral Vectors Containing a Cytokine Coding Sequence and a Heterologous Transcriptional Control Region FIG. 3 presents a schematic illustration of nonviral vectors containing a heterologous transcriptional control region operably linked to a cytokine coding sequence. In the figure, "TCR" indicates the heterologous transcriptional control region. The cytokine coding sequence is that of hIL-2. Operably linked to the hIL-2 coding sequence is a segment from the human growth hormone (hGH) gene that provides an intron and a polyadenylation signal sequence. The arrows indicate the direction of transcription from the transcriptional control region

Figure 4:
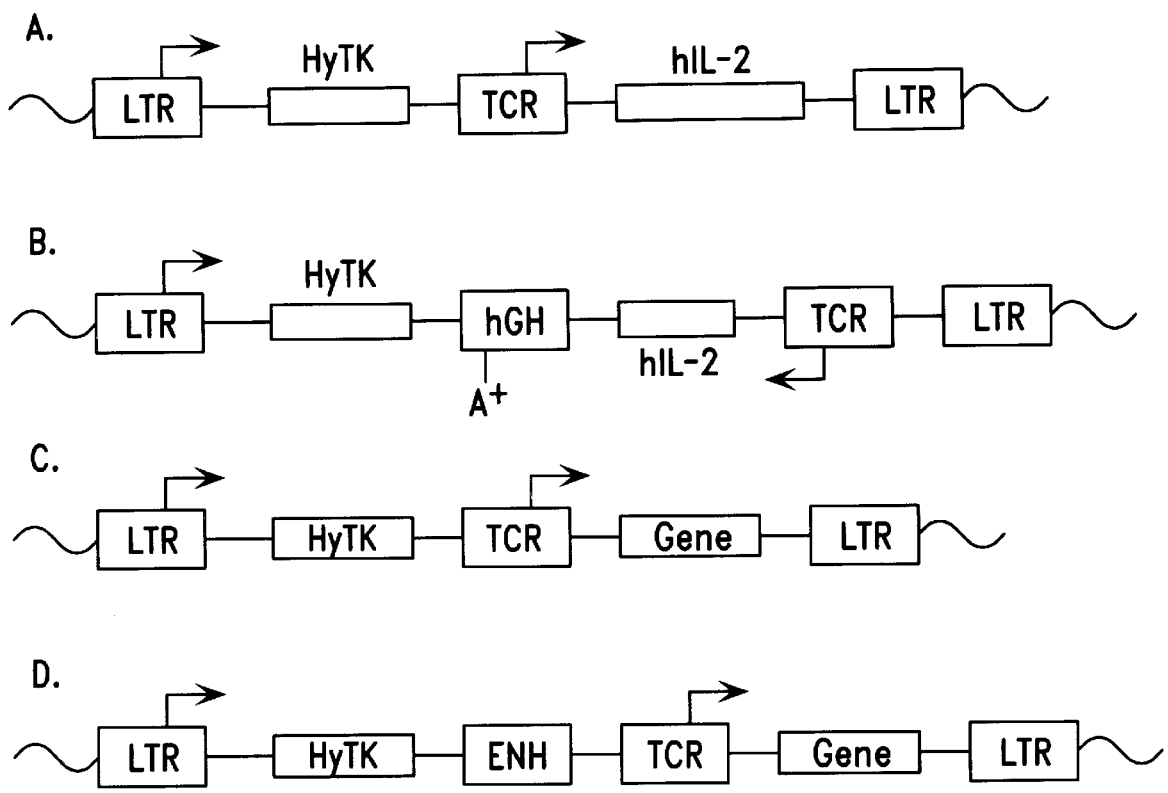
FIG. 4A and FIG. 4B present a schematic illustration of the proviral structures of retroviral vectors containing the HyTK coding sequence, and an hIL-2 sequence operably linked to a heterologous transcriptional control region.
FIG. 4C and FIG. 4D present a schematic illustration of the proviral structures of retroviral vectors containing the HyTK coding sequence, and a gene (which may be, for example, the CAT gene or the IL-2 gene) operably linked to a heterologous transcriptional control region. In the retroviral vector depicted in FIG. 4D, a heterologous enhancer sequence (which may be, for example, the CMV enhancer) is inserted upstream of the heterologous transcriptional control region.

EXAMPLE 7
Structure of Retroviral Vectors Containing a Cytokine Coding Sequence and a Heterologous Transcriptional Control Region FIG. 4 presents a schematic illustration of two types of retroviral vectors containing a heterologous transcriptional control region operably linked to a cytokine coding sequence. The vectors differ in the direction of transcription of the hIL-2 gene. In the figure, "TCR" indicates the heterologous transcriptional control region. The cytokine coding sequence is that of hIL-2. The symbols LTR and hGH are as described in the previous examples.

Figure 5:
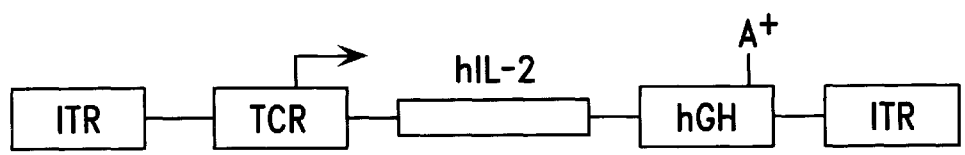
FIG. 5 presents a schematic illustration of an AAV vector containing a heterologous transcriptional control region operably linked to a cytokine coding sequence.

EXAMPLE 8
Structure of AAV Vectors Containing a Cytokine Coding Sequence and a Heterologous Transcriptional Control Region FIG. 5 presents a schematic illustration of one type of AAV vector containing a heterologous control transcriptional control region operably linked to a cytokine coding sequence. In the figure, "TCR" indicates the heterologous transcriptional control region. The cytokine coding sequence is that of hIL-2. "ITR" is an AAV inverted terminal repeat sequence. "hGH" is as described in the previous examples.

EXAMPLE 9
Preparation of T$_H$-Independent CD8+ CTL With A Vector Containing the IFN-γ Transcriptional Control Region Retroviral vectors are prepared from plasmids described in Example 4, except that the coding sequence for CAT is replaced by a coding sequence for hIL-2 and the transcriptional control region to which the coding region is operably linked is from the human IFN-γ gene. Preferably, the transcriptional control region also incorporates a heterologous enhancer, such as a CMV enhancer. These vectors are inserted into CMV-specific and HIV-specific CD8+ CTLs as prepared in Examples 1 and 2. The transduced CTLs and control CTLs are monitored for proliferation in the absence of T$_H$ cells and in the presence and absence of the amount of IL-2 required for proliferation of the control CTLs. Proliferation of transduced CTLs but not control CTLs in the presence of limiting amounts of added IL-2 is indicative of a lessened dependence on a T$_H$ cell stimulatory factor, IL-2.

The principles and teachings described above have been applied to produce additional embodiments, some of which are described below, further demonstrating the utility of this invention. Included, for example, are a number of additional vectors demonstrating the usefulness of activation-induced expression in various T lymphocytes, and an illustration of the growth of virus-specific cytotoxic T lymphocytes, in the absence of exogenously added IL-2, following transduction with vectors of this invention.

EXAMPLE 10
Activation-induced expression mediated by the lymphotoxin transcriptional control region, and the lymphotoxin transcriptional control region in combination with the CMV enhancer in human Jurkat T lymphocytes Plasmid constructions:

The proviral structure of the retroviral vector HyTK.lck-7.CAT is arranged as depicted in FIG. 4C, where "TCR" represents a small region encompassing the transcription start site from the murine lck gene, and "Gene" represents the CAT gene. HyTK.lck-7.CAT was constructed using standard techniques (Ausubel et al., 1987; full cite infra) as follows: A pair of overlapping oligonucleotides, 5'-TCGAGGGCTCAGAGGGAACCCAGTCAGGAGCT TGAATCCCACGATTCGGG-3 (SEQ ID NO:5) and 5'-GATCCCCGAATCGTGGGATTCAAGCTCCTGACT GGGTTCCCTCTGAGCCC-3'(SEQ ID NO:6), was annealed to form a 50-bp fragment spanning the transcription initiation site of the murine lck gene (Allen et. al, 1992) and ligated between XhoI and BamHI sites of pBluescript II KS+ (Stratagene) to create pKS/lck-7. The fragment was then excised from pKS/lck-7 using XhoI and BamHI, and ligated between the XhoI and BamHI sites of a derivative of tgLS(+)HyTK (Lupton et al., 1991) containing a CAT gene inserted downstream of the HyTK gene and unique HindIII, XhoI and BamHI sites 5' to the CAT gene, to create HyTK.lck-7.CAT. The minimal sequences inserted into HyTK.lck-7.CAT do not constitute a functional transcriptional control region, and this vector was included as a negative control to define the background levels of CAT activity.

The proviral structure of retroviral vector HyTK.CMV-.CAT is arranged as depicted in FIG. 4C, where "TCR" represents the CMV transcriptional control region, and "Gene" represents the CAT gene. HyTK.CMV.CAT was constructed using standard techniques (Ausubel et al., 1987) as follows: A fragment spanning the HCMV IE94 transcriptional control region (Boshart et al., 1985) was excised from HyTK.CMV.IL-2 (a derivative of tgLS(+)HyTK (Lupton et al., 1991) containing the HCMV IE94 transcriptional control region and a human IL-2 cDNA inserted downstream of the HyTK gene, in which HindIII and NheI sites flank the HCMV IE94 transcriptional control region) using HindIII and NheI, treated with the Klenow fragment of DNA polymerase I to render the ends blunt, and ligated between the HindIII and BamHI sites (that had also been treated with the Klenow fragment of DNA polymerase I) of HyTK.lck-7.CAT, thereby creating HyTK.CMV.CAT. The orientation of the CMV transcriptional control region was confirmed by restriction digestion. The CMV transcriptional control region is constitutively active in a wide variety of cell types, including T lymphocytes. In addition, the activity of the CMV transcriptional control region in T lymphocytes is increased upon T cell activation. HyTK.CMV.CAT was therefore included as a positive control.

The proviral structure of retroviral vector HyTK.LT.CAT is arranged as depicted in FIG. 4C, where "TCR" represents the lymphotoxin transcriptional control region, and "Gene" represents the CAT gene. HyTK.LT.CAT was constructed using standard techniques (Ausubel et al., 1987) as follows: The human LT transcriptional control region (Nedwin et al., 1985) was amplified directly from NotI-digested human genomic DNA by PCR using the oligonucleotides 5'-CACACAAAGCTTCTCGAAACTTCCTTTGTAGA-3' (SEQ ID NO:7) and 5'-CACACAGGATCCGGAGAG CCTCACCTGCTGTG-3' (SEQ ID NO:8). The PCR product was digested with BamHI and ligated into the BamHI site of HyTK.lck-7.CAT to create HyTK.LT.CAT. The orientation of the LT transcriptional control region was confirmed by restriction enzyme digestion.

The proviral structure of retroviral vector HyTK.CM-Ve.LT.CAT is arranged as depicted in FIG. 4D, where "TCR" represents the lymphotoxin transcriptional control region, "Gene" represents the CAT gene, and "ENH" represents the CMV enhancer. HyTK.CMVe.LT.CAT was constructed using standard techniques (Ausubel et al., 1987) as follows: A fragment spanning the HCMV IE94 enhancer was first amplified from a plasmid containing the HCMV IE94 transcriptional control region (Boshart et al., 1985) by PCR using the oligonucleotides 5'-ACACACAA GCTTATCGATGATCTCGAGGAGCTTGCCATTGC-3' (SEQ ID NO:9) and 5'-ACACACACAAGCTTAGAC CTCCCACCGTACACGCCTAC-3' (SEQ ID NO:10). The PCR product was digested with HindIII and ligated into the unique HindIII site of HyTK.hPerf.CAT (a derivative of tgLS(+)HyTK (Lupton et al., 1991) containing the human perforin transcriptional control region and a CAT gene inserted downstream of the HyTK gene, and a unique HindIII site 5' to the perforin transcriptional control region) to create HyTK.CMVe.hPerf.CAT. The fragment spanning the HCMV IE94 enhancer was then excised from HyTK.C-MVe.hPerf.CAT using HindIII and ligated into the HindIII site of HyTK.LT.CAT upstream of the LT transcriptional control region to create HyTK.CMVe.LT.CAT. The orientation of the enhancer was confirmed by restriction enzyme digestion.

Human Jurkat T lymphocytes were grown in RPMI 1640 medium supplemented with 10% fetal bovine serum, 0.1 mM non-essential amino acids, 50 $\mu$M 2-mercaptoethanol, 2 mM L-glutamine, 50 U/ml penicillin, and 50 $\mu$g/ml streptomycin at 37° C. in a humidified atmosphere supplemented with 5% $CO_2$. Aliquots of cells ($4 \times 10^6$) were electroporated with 10 $\mu$g of HyTK.CMV.CAT, HyTK.lck-7.CAT, HyTK.LT.CAT or HyTK.CMVe.LT.CAT plasmid DNA in 0.8-ml of complete medium using a 0.4 cm cuvette and a Biorad Gene Pulser set at 300 V and 960 $\mu$F. Following electroporation, the cells were returned to culture and incubated for 18 h. The cultures were then supplemented with 350 $\mu$g/ml of hygromycin B to select for the transfected cells. The cells were collected by centrifugation and resuspended in fresh medium containing 350 $\mu$g/ml of hygromycin B every 3–4 d. After 21–28 d the selected cells were activated and assayed for CAT activity, as described below.

To activate the transfected cells, the cultures were supplemented with 10 ng/ml of PMA and 500 ng/ml of ionomycin. At 0 h, 4 h, 8 h, 24 h, 32 h and 48 h after activation, the cells were harvested and CAT extracts were prepared and assayed using standard techniques (Ausubel et al., 1987) as follows: The transfected cells were harvested by centrifugation, resuspended in 100 $\mu$l of 0.25M Tris (pH 8.0), and subjected to 3 cycles of freezing (−20° C. for 5 min) and thawing (37° C. for 5 min). Cell debris was pelleted by centrifugation, and the supernatant was transferred to a clean tube. A 50 $\mu$l aliquot of extract was mixed with 78 $\mu$l of 0.5M Tris (pH 8.0), 20 $\mu$l of 24 mM acetyl coenzyme A, and 2 $\mu$l of [14C]-labeled chloramphenicol, and the mixture incubated at 37° C. for 20–24 h. The reaction was extracted with 1 ml of ethyl acetate, the ethyl acetate extract was evaporated to dryness, and resuspended in 30 $\mu$l of ethyl acetate. The extract was then applied to a thin layer chromatogram, which was developed in a mixture of 95% chloroform/5% methanol. The chromatogram was then exposed to X ray film, or visualized using a phosphorimager.

Figure 6:
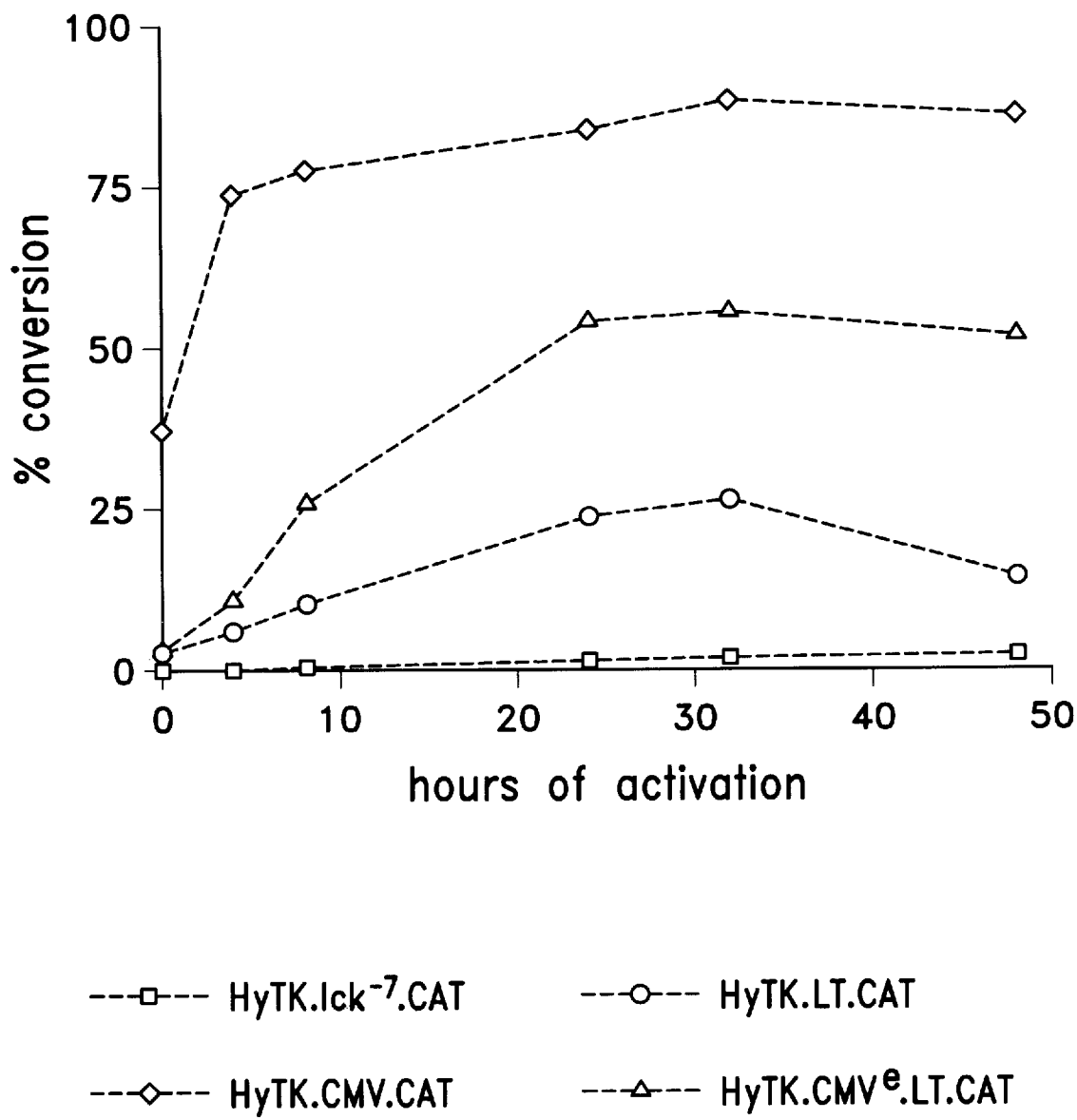
FIG. 6 is a line graph depicting the time course of CAT activity expressed by human Jurkat T lymphocytes transfected with the vectors listed in the legend, after activation with PMA and ionomycin, as described in Example 10.

As shown in FIG. 6, cells transfected with the negative control vector, HyTK.lck-7.CAT, did not express significant levels of CAT activity. Cells transfected with the positive control vector, HyTK.CMV.CAT, constitutively expressed CAT activity and the level of expression was increased upon T cell activation. Cells transfected with HyTK.LT.CAT or HyTK.CMVe.LT.CAT, and left unactivated, did not express significant levels of CAT activity. However, cells transfected with HyTK.LT.CAT or HyTK.CMVe.LT.CAT expressed significant levels of CAT activity following activation with PMA and ionomycin. HyTK.CMVe.LT.CAT expressed substantially more CAT activity than did HyTK.LT.CAT following activation with PMA and ionomycin.

The results demonstrate that the LT transcriptional control region and the LT transcriptional control region in combination with the CMV enhancer mediate activation-induced expression in human T lymphocytes, and that the CMV enhancer may be used to enhance the level of activation-induced expression from the LT transcriptional control region in human T lymphocytes. The results further demonstrate that the LT transcriptional control region and the LT transcriptional control region in combination with the CMV enhancer are functional in human T lymphocytes when inserted into a retroviral vector.

EXAMPLE 11

Activation-induced expression mediated by the IL-2R$\alpha$ transcriptional control region in combination with the CMV enhancer in human Jurkat T lymphocytes Plasmid constructions:

Plasmids HyTK.lck-7.CAT and HyTK.CMV.CAT were constructed as in Example 10.

The proviral structure of retroviral vector HyTK.IL-2R$\alpha$.CAT is arranged as depicted in FIG. 4C, where "TCR" represents the IL-2R$\alpha$ transcriptional control region, and "Gene" represents the CAT gene. HyTK.IL-2R$\alpha$.CAT was constructed using standard techniques (Ausubel et al., 1987) as follows: The human IL-2R$\alpha$ transcriptional control region (Cross et al., 1987) was amplified directly from NotI-digested human genomic DNA by PCR using the oligonucleotides 5'-CACACAAAGCTTGACTCCTGA GGACGTTACAG-3' )SEQ ID NO:11) and 5'-CACA CAGGATCCGGGCTGTCACCCTTGTGGGT-3' (SEQ ID NO:12). The PCR product was digested with HindIII and BamHI and ligated between the HindIII and BamHI sites of HyTK.lck-7.CAT to create HyTK.IL-2R$\alpha$.CAT. The orientation of the IL-2R$\alpha$ transcriptional control region was confirmed by restriction enzyme digestion and DNA sequencing.

The proviral structure of retroviral vector HyTK.CMVe.IL-2R$\alpha$.CAT is arranged as depicted in FIG. 4D, where "TCR" represents the IL-2R$\alpha$ transcriptional control region, "Gene" represents the CAT gene, and "ENH" represents the CMV enhancer. HyTK.CMVe.IL-2R$\alpha$.CAT was constructed using standard techniques (Ausubel et al., 1987) as follows: A fragment spanning the HCMV IE94 enhancer was excised from HyTK.CMVe.hPerf.CAT (see Example 10) using HindIII and ligated into the HindIII site of HyTK.IL-2R$\alpha$.CAT upstream of the IL-2R$\alpha$.CAT. The orientation of the enhancer was confirmed by restriction enzyme digestion.

Human Jurkat T lymphocytes were grown and transfected as described in Example 10, except that the cells were transfected with 10 $\mu$g of HyTK.CMV.CAT, HyTK.lck-7.CAT, HyTK.IL-2R$\alpha$.CAT or HyTK.CMVe.IL-2R$\alpha$.CAT plasmid DNA. Preparation and assay of CAT extracts was conducted as described in Example 10.

Figure 7:
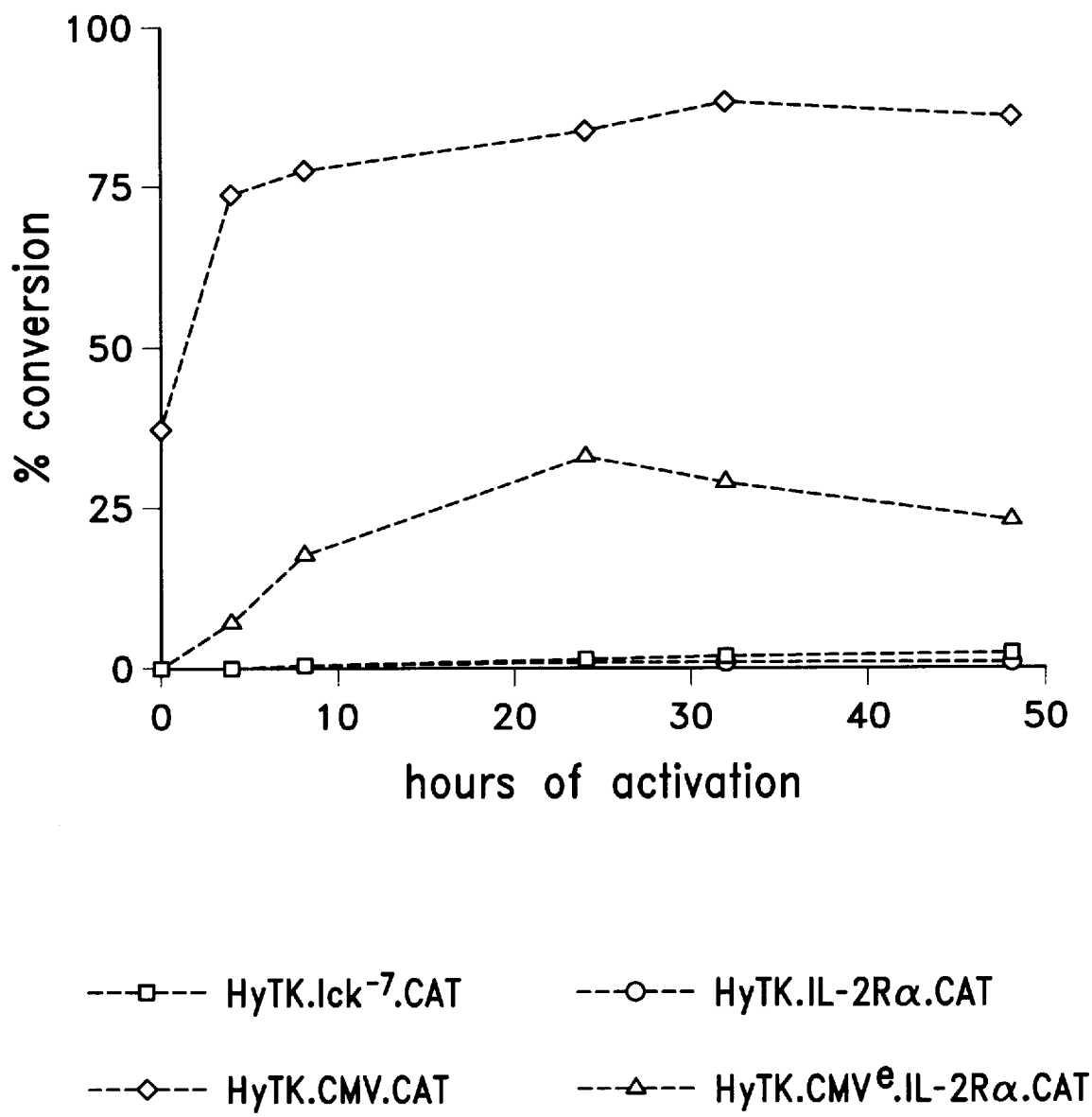
FIG. 7 is a line graph depicting the time course of CAT activity expressed by human Jurkat T lymphocytes transfected with the vectors listed after activation with PMA and ionomycin, as described in Example 11.

As shown in FIG. 7, cells transfected with the negative control vector, HyTK.lck-7.CAT did not express significant levels of CAT activity. Cells transfected with the positive control vector, HyTK.CMV.CAT, constitutively expressed CAT activity and the level of expression was increased upon T cell activation. Cells transfected with HyTK.IL-2R$\alpha$.CAT or HyTK.CMVe.IL-2R$\alpha$.CAT, and left unactivated, did not express significant levels of CAT activity. Cells transfected with HyTK.IL-2R$\alpha$.CAT did not express significant levels of CAT activity following activation with PMA and ionomycin. However, cells transfected with HyTK.CMVe.IL-2Rα.CAT expressed significant levels of CAT activity following activation with PMA and ionomycin.

The results demonstrate that the IL-2Rα transcriptional control region in combination with the CMV enhancer mediates activation-induced expression in human T lymphocytes, and that the CMV enhancer may be used to enhance the level of activation-induced expression from the IL-2Rα transcriptional control region in human T lymphocytes. The results further demonstrate that the IL-2Rα transcriptional control region in combination with the CMV enhancer is functional in human T lymphocytes when inserted into a retroviral vector.

EXAMPLE 12

Activation-induced expression mediated by the lymphotoxin transcriptional control region in combination with the CMV enhancer, and the IL-2Rα transcriptional control region in combination with the CMV enhancer in human peripheral blood T lymphocytes Plasmids were constructed as in Example 10 and Example 11.

Human peripheral blood T lymphocytes were prepared as follows. Human peripheral blood was collected by venipuncture from healthy volunteers and mixed with an equal volume of RPMI 1640 medium. A 35-ml aliquot was layered over 14 ml of isolymph in a 50-ml conical tube and centrifuged at 2000 rpm for 20 min at 20° C. in a Sorvall RT6000D benchtop centrifuge. The cells at the interface were pelleted by centrifuging at 1600 rpm for 10 min at 4° C. in a Sorvall RT6000D benchtop centrifuge, washed three times by resuspending in complete medium (RPMI 1640 medium supplemented with 10% fetal bovine serum, 0.1 mM non-essential amino acids, 50 $\mu$M 2-mercaptoethanol, 2 mM L-glutamine, 50 U/ml penicillin, and 50 $\mu$g/ml streptomycin) and centrifuging at 1600 rpm for 10 min at 4° C. in a Sorvall RT6000D benchtop centrifuge, and then resuspended in 10 nil of complete medium. A 0.3 ml aliquot of AET-SRBC (AET-treated sheep red blood cells, as described in Currents Protocols in Immunology, J. E. Coligan et al., eds., 1991) was added, the suspension was mixed gently, centrifuged at the slowest centrifuge speed for 5 min at 20° C. in a Sorvall RT6000D benchtop centrifuge and incubated at room temperature for 20 min. The cell pellet was then resuspended by shaking gently, and the mixture was layered over 14 ml of isolymph in a 50 ml conical tube and centrifuged at 2000 rpm for 20 min at 20° C. in a Sorvall RT6000D benchtop centrifuge. The supernatant was removed and the cells were resuspended in 10 ml of complete medium. A second 0.3-ml aliquot of AET-SRBC was added, the suspension was mixed gently, centrifuged at the slowest centrifuge speed for 5 min at 20° C. in a Sorvall RT6000D benchtop centrifuge, and incubated at room temperature for 20 min. The cell pellet was then resuspended by shaking gently, and the mixture was layered over 14 ml of isolymph in a 50 ml conical tube and centrifuged at 2000 rpm for 20 min at 20° C. in NH$_4$Cl lysing medium that had been prewarmed to 37° C. and incubated until lysis of the red blood cells was apparent. The mixture was then centrifuged at 1400 rpm for 8 min at 20° C. in a Sorvall RT6000D benchtop centrifuge. The pelleted cells were washed twice by resuspending in complete medium and centrifuging at 1600 rpm for 10 min at 4° C. in a Sorvall RT6000D benchtop centrifuge, and resuspended at a density of 5×10$^5$ cell/ml in complete medium. PHA was added to a concentration of 1% and the cells were placed in T-75 flasks and incubated at 37° C. in a humidified atmosphere supplemented with 5% CO$_2$ for 8 d. The cells were then pelleted by centrifuging at 1600 rpm for 10 min at 4° C. in a Sorvall RT6000D benchtop centrifuge, washed once by resuspending in complete medium and centrifuging at 1600 RPM for 10 min at 4° C. in a Sorvall RT6000D benchtop centrifuge, and resuspended in complete medium at a density of 5×10$^6$ cells/ml. Aliquots of cells (4×10$^6$) were electroporated with 10 $\mu$g of HyTK.CMV.CAT, or 50 $\mu$g of HyTK.lck-7.CAT, HyTK.CMVe.LT.CAT or HyTK.CMVe.IL-2Rα.CAT plasmid DNA in 0.8 ml of complete medium using a 0.4 cm cuvette and a Biorad Gene Pulser set at 350 V and 960 $\mu$F. Following electroporation, the cells were returned to culture and incubated for 1–2 h.

To activate the transfected cells, the cultures were supplemented with 10 ng/ml of PMA and 500 ng/ml of ionomycin. At 24 h after activation, the cells were harvested and CAT extracts were prepared and assayed using standard techniques (Ausubel et al., 1987) as follows: The transfected cells were harvested by centrifugation, resuspended in 100 $\mu$l of 0.25 Tris (pH 8.0), and subjected to 3 cycles of freezing (–20° C. for 5 min) and thawing (37° C. for 5 min). Cell debris was pelleted by centrifugation, and the supernatant was transferred to a clean tube. A 50-$\mu$l aliquot of extract was mixed with 78 $\mu$l of 0.5M Tris (pH 8.0), 20 $\mu$l of 24 mM acetyl coenzyme A, and 2 $\mu$l of [$^{14}$C]-labeled chloramphenicol, and the mixture incubated at 37° C. for 20–24 h. The reaction was extracted with 1 ml of ethyl acetate, the ethyl acetate extract was evaporated to dryness and resuspended in 30 $\mu$l of ethyl acetate. The extract was then applied to a thin-layer chromatogram, which was developed in a mixture of 95% chloroform/5% methanol. The chromatogram was then exposed to X-ray film, or visualized using a phosphorimager.

Figure 8:
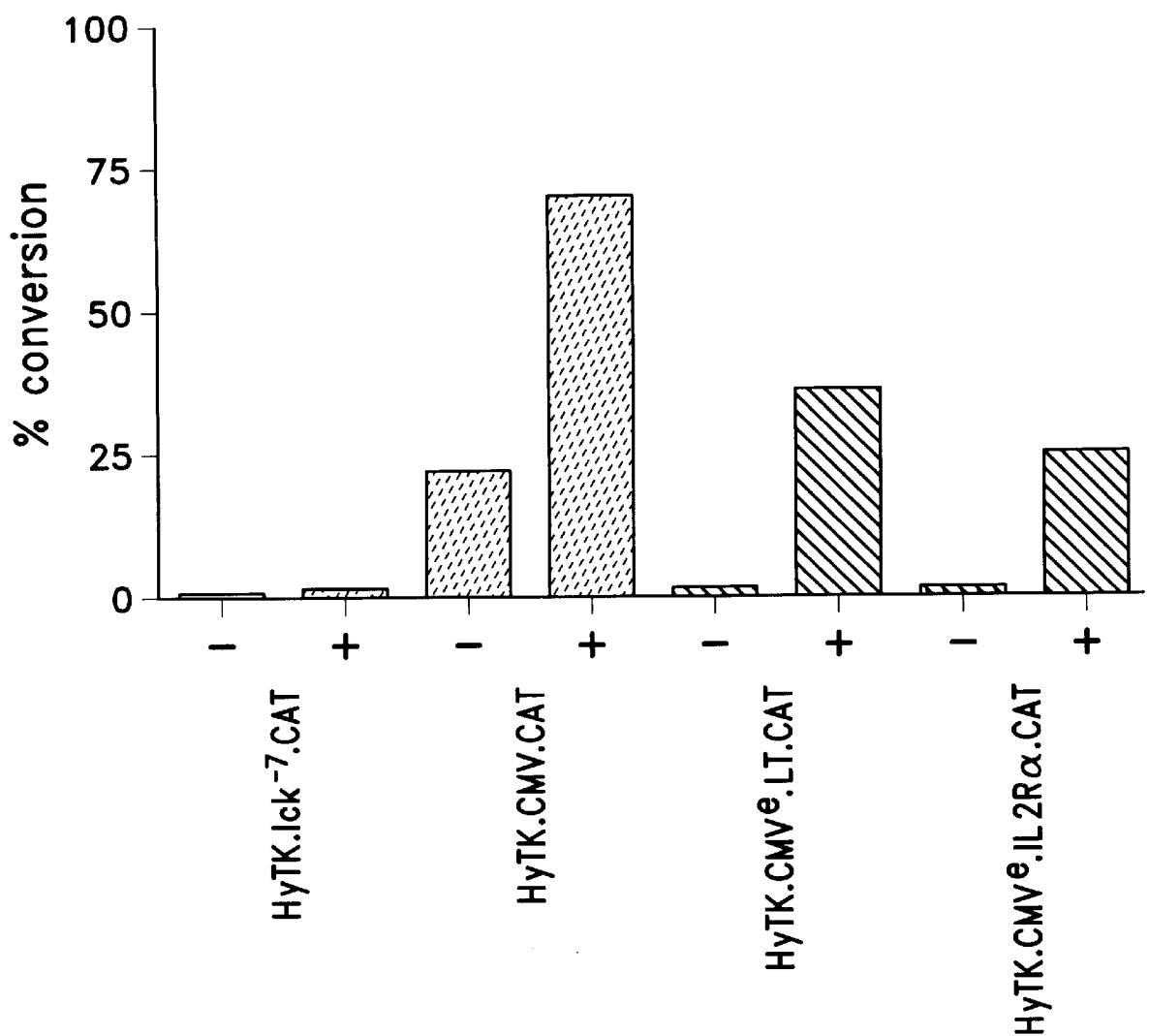
FIG. 8 is a bar graph depicting the level of CAT activity expressed by human peripheral T lymphocytes transfected with the vectors listed, with (+) or without (−) activation with PMA and ionomycin, as described in Example 12.

As shown in FIG. 8, cells transfected with the negative control vector, HyTK.lck-7.CAT and left unactivated (–) or activated (+) did not express significant levels of CAT activity. Cells transfected with the positive control vector, HyTK.CMV.CAT, and left unactivated (–) constitutively expressed CAT activity and the level of expression was increased upon T cell activation (+). Cells transfected with HyTK.CMVe.LT.CAT or HyTK.CMVe.IL-2Rα.CAT and left unactivated (–) did not express significant levels of CAT activity. However, cells transfected with HyTK.CMVe.LT..CAT or HyTK.CMVe.IL-2Rα.CAT expressed significant levels of CAT activity following activation for 24 h (+).

The results demonstrate that the LT transcriptional control region in combination with the CMV enhancer and the IL-2Rα transcriptional control region in combination with the CMV enhancer mediate activation-induced expression in human T lymphocytes. The results further demonstrate that the LT transcriptional control region in combination with the CMV enhancer and the IL-2Rα transcriptional control region in combination with the CMV enhancer are functional in human T lymphocytes when inserted into a retroviral vector.

EXAMPLE 13

Activation-induced expression mediated by the IL-4 transcriptional control region in combination with the CMV enhancer in human Jurkat T lymphocytes Plasmids HyTK.lck-7.CAT and HyTK.CMV.CAT were constructed as in Example 10.

Plasmid HyTK.IL-4.CAT was constructed as in example 4. The proviral structure of retroviral vector HyTK.CMVe.IL-4.CAT is arranged as depicted in FIG. 4D, where "TCR" represents the IL-4 transcriptional control region, "Gene" represents the CAT gene, and "ENH" represents the CMV enhancer. HyTK.CMVe.IL-4.CAT was constructed using standard techniques (Ausubel et al., 1987)

as follows: A fragment spanning the HCMV IE94 enhancer was excised from HyTK.CMVe.hPerf.CAT (see Example 10) using HindIII and ligated into the HindIII site of HyTK.IL-4.CAT upstream of the IL-4 transcriptional control region to create HyTK.CMVe.IL-4.CAT. The orientation of the enhancer was confirmed by restriction enzyme digestion.

Human Jurkat T lymphocytes were grown as described in Example 10. Aliquots of cells (4×10$^6$) were electroporated with 25 µg of HyTK.CMV.CAT, HyTK.lck-7.CAT, HyTK.IL-4.CAT or HyTK.CMVe.IL-4.CAT plasmid DNA in 0.8-ml of complete medium using a 0.4 cm cuvette and a Biorad Gene Pulser set at 300 V and 960 µF. Following electroporation, the cells were returned to culture and incubated for 2 d. The cultures were then supplemented with 350 µg/ml of hygromycin B to select for the transfected cells. The cells were collected by centrifugation and resuspended in fresh medium containing 350 µg/ml of hygromycin B every 3–4 d. After 14–21 d the selected cells were activated and assayed for CAT activity.

CAT extracts were prepared and assayed as described in Example 10, except that the cells were activated with PMA and ionomycin for 0 h, 3 h, 6 h, or 24 h.

Figure 9:
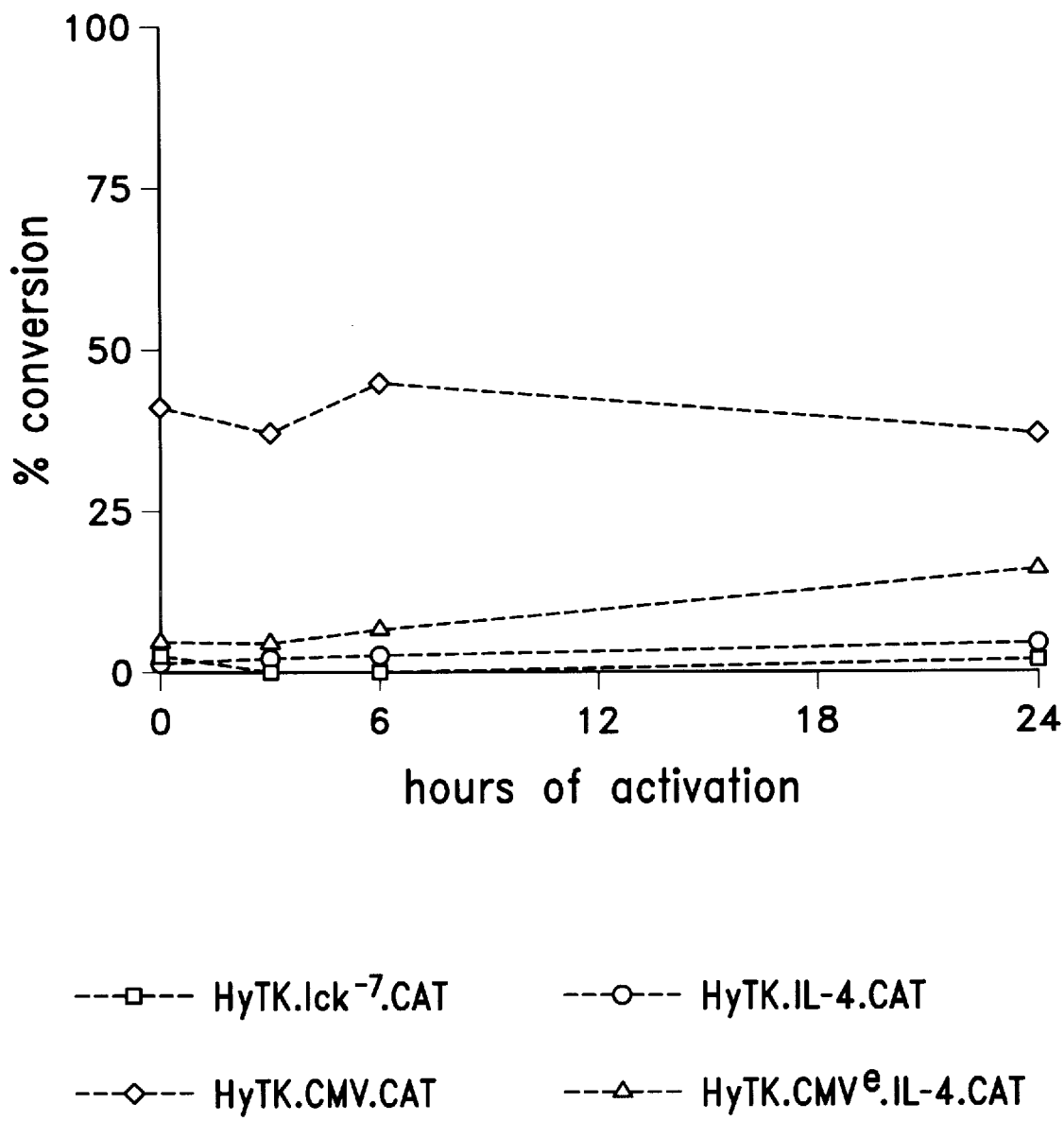
FIG. 9 is a line graph depicting the time course of CAT activity expressed by human Jurkat T lymphocytes transfected with the vectors listed, with or without activation with PMA and ionomycin, as described in Example 13.

As shown in FIG. 9, cells transfected with the negative control vector, HyTK.lck-7.CAT, did not express significant levels of CAT activity. Cells transfected with the positive control vector, HyTK.CMV.CAT, constitutively expressed CAT activity. Cells transfected with HyTK.IL-4.CAT or HyTK.CMVe.IL-4.CAT, and left unactivated, did not express significant levels of CAT activity following activation with PMA and ionomycin. However, cells transfected with HyTK.CMVe.IL-4.CAT expressed significant levels of CAT activity following activation with PMA and ionomycin.

The results demonstrate that the IL-4 transcriptional control region in combination with the CMV enhancer mediates activation-induced expression of human T lymphocytes, and that the CMV enhancer may be used to enhance the level of activation-induced expression from the IL-4 transcriptional control region in human T lymphocytes. The results further demonstrate that the IL-4 transcriptional control region in combination with the CMV enhancer is functional in human T lymphocytes when inserted into a retroviral vector.

EXAMPLE 14
Activation-induced expression mediated by the IL-3 transcriptional control region, and the IL-3 transcriptional control region in combination with the CMV enhancer in human Jurkat T lymphocytes Plasmids HyTK.lck-7.CAT and HyTK.CMV.CAT were constructed as in Example 10.

Plasmid HyTK.hIL-3.CAT was constructed as in example 4.

The proviral structure of retroviral vector HyTK.CMVe.hIL-3.CAT is arranged as depicted in FIG. 4D, where "TCR" represents the IL-3 transcriptional control region, "Gene" represents the CAT gene, and "ENH" represents the CMV enhancer. HyTK.CMVe.hIL-3.CAT was constructed using standard techniques (Ausubel et al., 1987) as follows: A fragment spanning the HCMV IE94 enhancer was excised from HyTK.CMVe.hPerf.CAT (see Example 10) using HindIII and ligated into the HindIII site of HyTK.IL-3.CAT upstream of the IL-3 transcriptional control region to create HyTK.CMVe.IL-3.CAT. The orientation of the enhancer was confirmed by restriction enzyme digestion.

Human Jurkat T lymphocytes were grown as described in Example 13, except that the cells were transfected with 10 µg of HyTK.CMV.CAT, HyTK.lck-7.CAT, HyTK.IL-3.CAT or HyTK.CMVe.IL-3.CAT plasmid DNA.

Preparation and assay of CAT extracts was carried out as described in Example 13.

Figure 10:
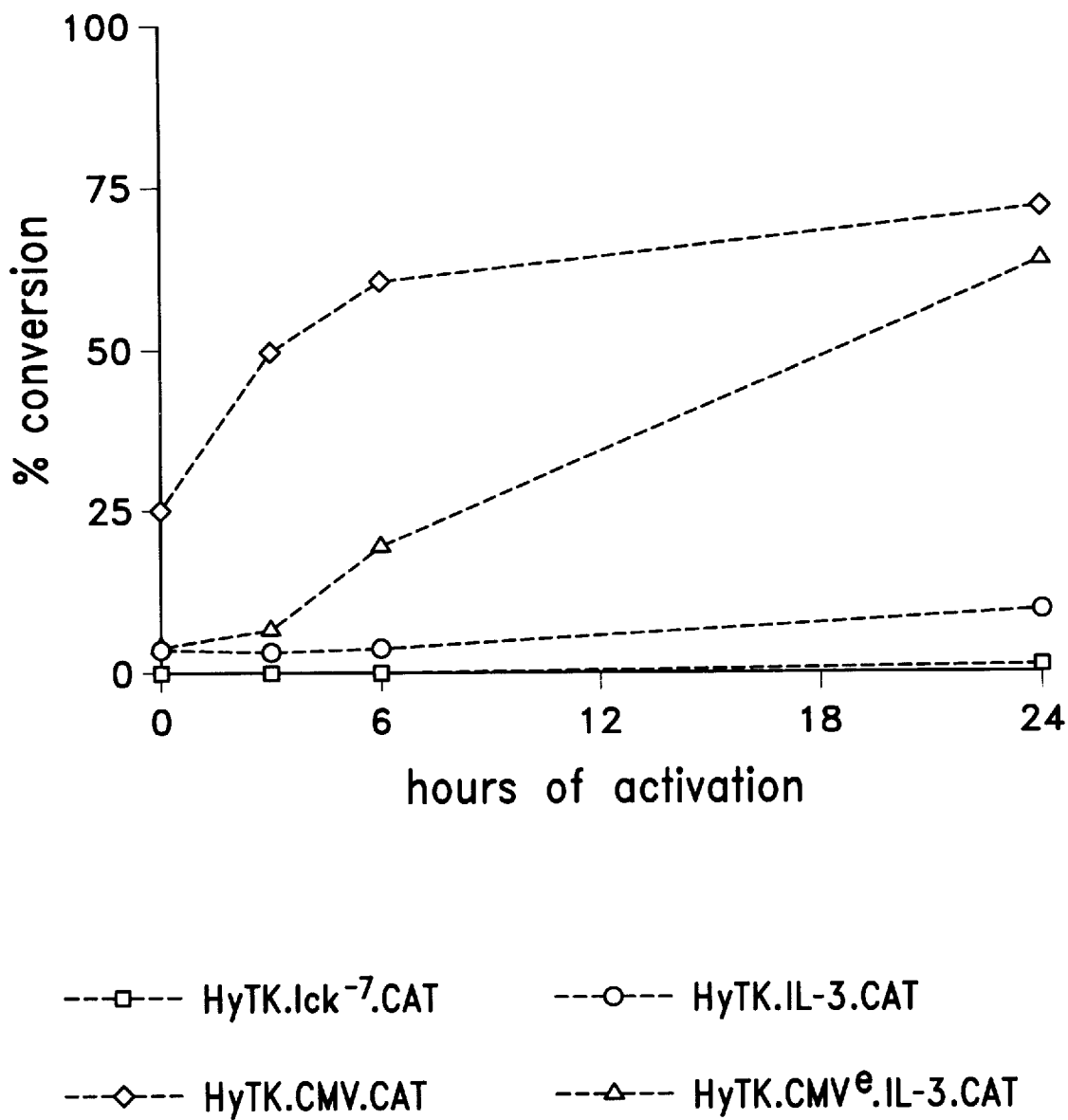
FIG. 10 is a line graph depicting the time course of CAT activity expressed by human Jurkat T lymphocytes transfected with the vectors listed, with or without activation with PMA and ionomycin, as described in Example 14.

As shown in FIG. 10, cells transfected with the negative control vector, HyTK.lck-7.CAT, did not express significant levels of CAT activity. Cells transfected with the positive control vector, HyTK.CMV.CAT, constitutively expressed CAT activity and the level of expression was increased upon T cell activation. Cells transfected with HyTK.hIL-3.CAT or HyTK.CMVe.hIL-3.CAT, and left unactivated, did not express significant levels of CAT activity. However, cells transfected with HyTK.hIL-3.CAT or HyTK.CMVe.hIL-3.CAT expressed significant levels of CAT activity following activation with PMA and ionomycin. HyTK.CMVe.hIL-3.CAT expressed substantially more CAT activity than did HyTK.hIL-3.CAT following activation with PMA and ionomycin.

The results demonstrate that the hIL-3 transcriptional control region and the hIL-3 transcriptional control region in combination with the CMV enhancer mediate activation-induced expression in human T lymphocytes, and that the CMV enhancer may be used to enhance the level of activation-induced expression from the IL-3 transcriptional control region in human T lymphocytes. The results further demonstrate that the IL-3 transcriptional control region and the IL-3 transcriptional control region in combination with the CMV enhancer are functional in human T lymphocytes when inserted into a retroviral vector.

EXAMPLE 15
Activation-induced expression mediated by the CTLA-1 transcriptional control region, and the CTLA-1 transcriptional control region in combination with the CMV enhancer in human Jurkat T lymphocytes Plasmids HyTK.lck-7.CAT and HyTK.CMV.CAT were constructed as in Example 10.

The proviral structure of retroviral vector HyTK.CTLA-1.CAT is arranged as depicted in FIG. 4C, where "TCR" represents the CTLA-1 transcriptional control region and "Gene" represents the CAT gene. HyTK.CTLA-1.CAT was constructed using standard techniques (Ausubel et al., 1987) as follows: The human CTLA-1 transcriptional control region (Heusel et al., 1991) was amplified directly from human genomic DNA by PCR using the oligonucleotides 5α-CACACACAAGCTTCTATATTTTGAGATATACCAT TCCTCA-3' (SEQ ID NO:13) and 5'-ACACACACGG ATCCAGGAAGGCTGCCCTGGTTGGAGCTGCT-3' (SEQ ID NO:14). The PCR product was digested with HindIII and BamHI and ligated between the HindIII and BamHI sites of HyTK.lck-7.CAT to created HyTK.CTLA-1.CAT. The orientation of the CTLA-1 transcriptional control region was confirmed by restriction enzyme digestion and DNA sequencing.

The proviral structure of retroviral vector HyTK.CMVe.CTLA-1.CAT is arranged as depicted in FIG. 4D, where "TCR" represents the CTLA-1 transcriptional control region, "Gene" represents the CAT gene, and "ENH" represents the CMV enhancer. HyTK.CMVe.CTLA-1.CAT was constructed using standard techniques (Ausubel et al., 1987) as follows: A fragment spanning the HCMV IE94 enhancer was excised from HyTK.CMVe.hPerf.CAT (see Example 10) using HindIII and ligated into the HindIII site of HyTK.CTLA-1.CAT upstream of the CTLA-1 transcriptional control region to create HyTK.CMVe.CTLA-1.CAT. The orientation of the enhancer was confirmed by restriction enzyme digestion.

Human Jurkat T lymphocytes were grown and transfected as described in Example 13, except that the cells were transfected with 10 µg of HyTK.CMV.CAT, HyTK.lck- 7.CAT, HyTK.CTLA-1.CAT or HyTK.CMVe.CTLA-1.CAT plasmid DNAs.

Preparation and assay of CAT extracts was carried out as described in Example 13.

Figure 11:
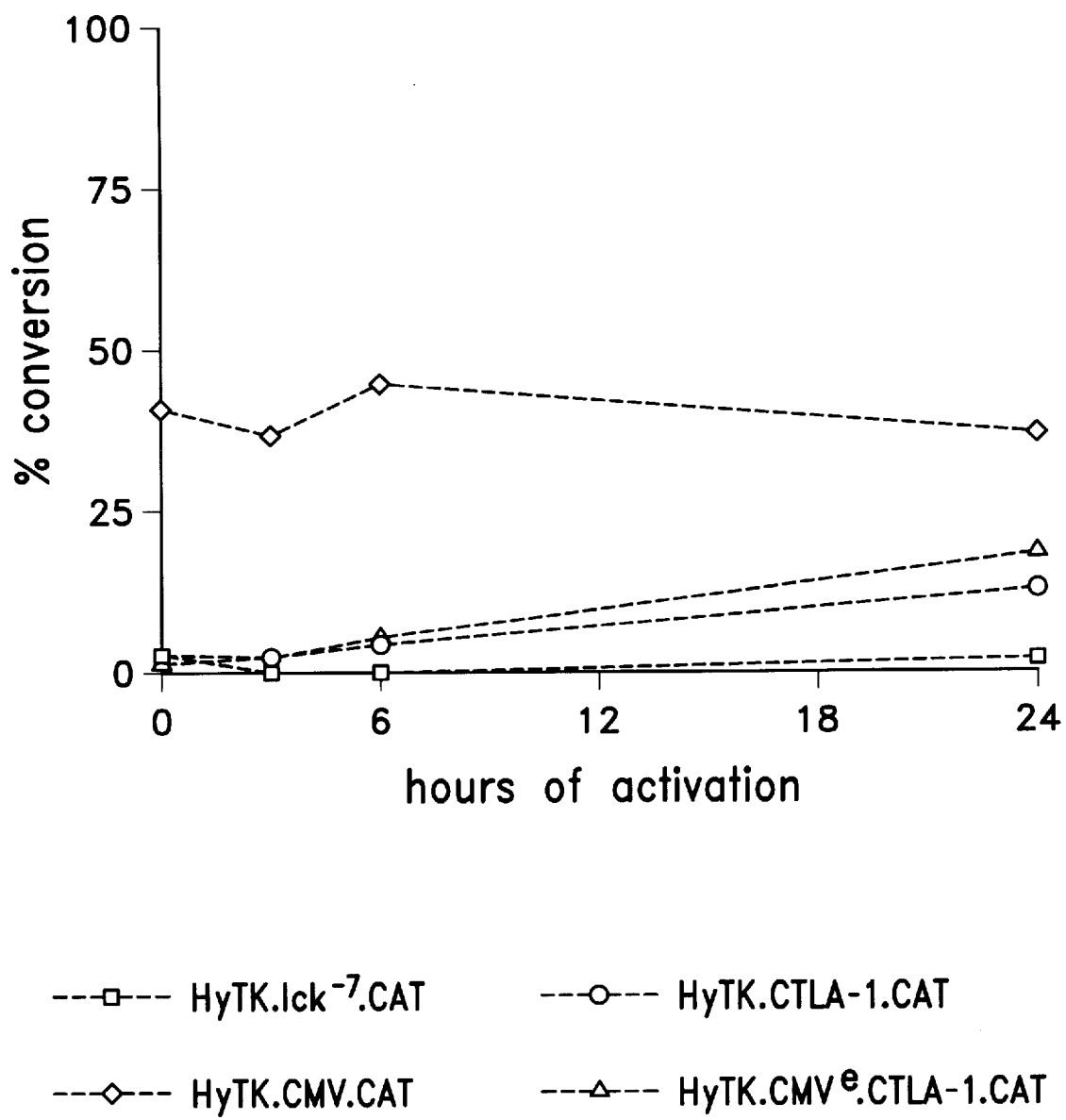
FIG. 11 is a line graph depicting the time course of CAT activity expressed by human Jurkat T lymphocytes transfected with the vectors listed, with or without activation with PMA and ionomycin, as described in Example 15.

As shown in FIG. 11, cells transfected with the negative control vector, HyTK.lck-7.CAT, did not express significant levels of CAT activity. Cells transfected with the positive control vector, HyTK.CMV.CAT, constitutively expressed CAT activity and the level of expression was increased upon T cell activation. Cells transfected with HyTK.CTLA-1.CAT or HyTK. CMVe.CTLA-1.CAT, and left unactivated, did not express significant levels of CAT activity. However, cells transfected with HyTK.CTLA-1.CAT or HyTK.CMVe.CTLA-1.CAT expressed significant levels of CAT activity following activation with PMA and ionomycin.

The results demonstrate that the CTLA-1 transcriptional control region and the CTLA-1 transcriptional control region in combination with the CMV enhancer mediate activation-induced expression in human T lymphocytes. The results further demonstrate that the CTLA-1 transcriptional control region and the CTLA-1 transcriptional control region in combination with the CMV enhancer are functional in human T lymphocytes when inserted into a retroviral vector.

EXAMPLE 16

Activation-induced expression mediated by the IL-3 transcriptional control region in combination with the CMV enhancer, and the CTLA-1 transcriptional control region in combination with the CMV enhancer in human peripheral blood T lymphocytes Plasmids were constructed as in Examples 14 and 15.

Human peripheral blood T cells were prepared and transfected as in Example 12, except that the cells were transfected with 50 µg of HyTK.CMV.CAT, HyTK.lck-7.CAT, HyTK.CMVe.IL-3.CAT or HyTK.CMVe.CTLA-1.CAT plasmid DNA.

The transfected cells were activated and CAT extracts were prepared and assayed a described in Example 12, except that the transfected cells were incubated for 3 h before activation, and extracts were prepared after 20 h of activation.

Figure 12:
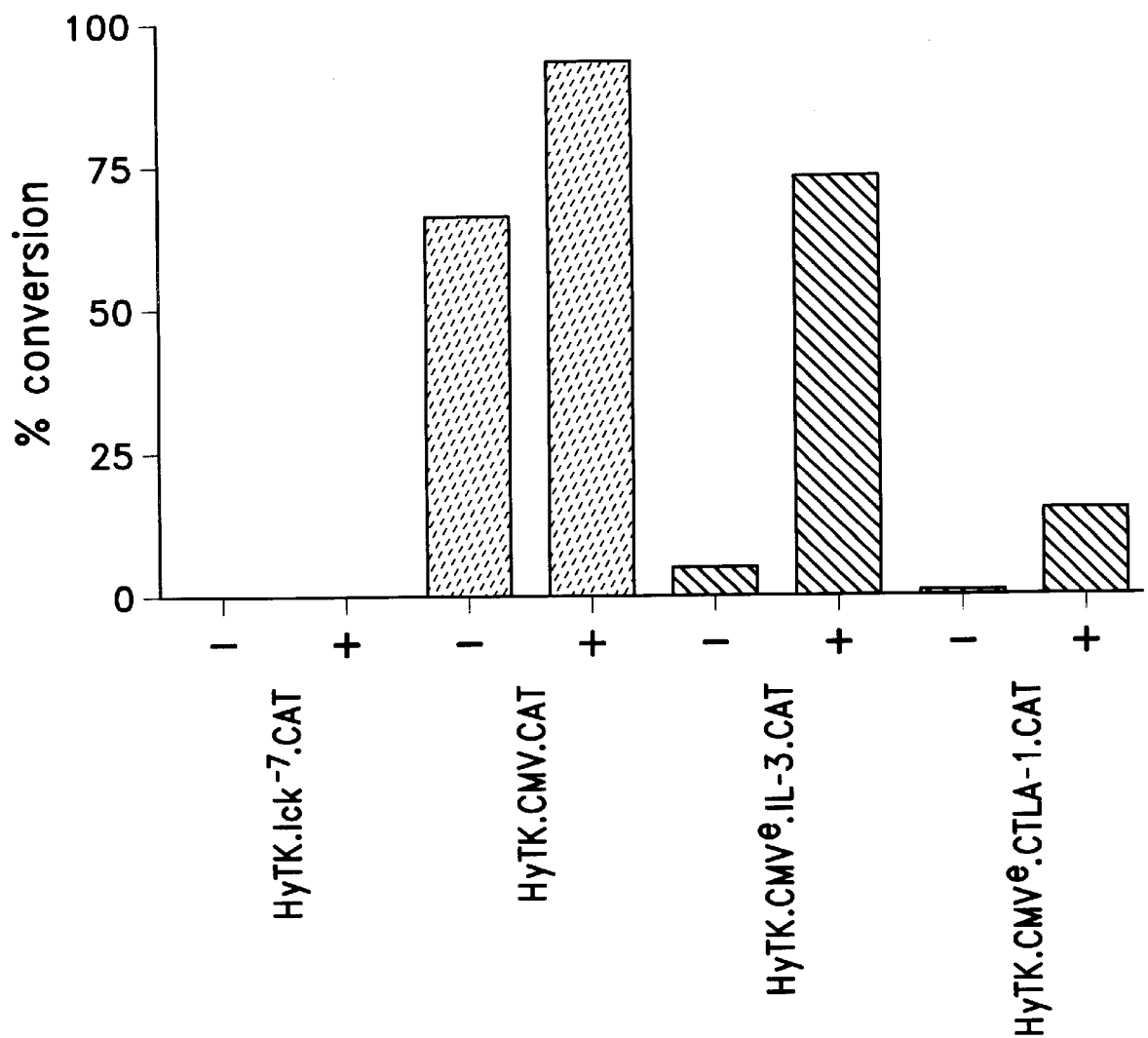
FIG. 12 is a bar graph depicting the level of CAT activity expressed by human peripheral T lymphocytes transfected with the vectors listed, with (+) or without (-) activation with PMA and ionomycin, as described in Example 16.

As shown in FIG. 12, cells transfected with the negative control vector, HyTK.lck-7.CAT, and left unactivated (−) or activated (+) did not express significant levels of CAT activity. Cells transfected with the positive control vector, HyTK.CMV.CAT, and left unactivated (−) constitutively expressed CAT activity and the level of expression was increased upon T cell activation (+). Cells transfected with HyTK.CMVe.IL-3.CAT or HyTK.CMVe.CTLA-1.CAT and left unactivated (−), did not express significant levels of CAT activity. However, cells transfected with HyTK.CMVe.IL-3.CAT or HyTK.CMVe.CTLA-1.CAT expressed significant levels of CAT activity following activation for 24 h (+).

The results demonstrate that the IL-3 transcriptional control region in combination with the CMV enhancer and the CTLA-1 transcriptional control region in combination with the CMV enhancer mediate activation-induced expression in human T lymphocytes. The results further demonstrate that the IL-3 transcriptional control region in combination with the CMV enhancer and the CTLA-1 transcriptional control region in combination with the CMV enhancer are functional in human T lymphocytes when inserted into a retroviral vector.

Example 17

Activation-induced expression mediated by the γ-IFN transcriptional control region in combination with the CMV enhancer in human Jurkat T lymphocytes Plasmid constructions:

Plasmid HyTK.CMV.CAT was constructed as in Example 10.

The proviral structure of the retroviral vector HyTK.CMVe.γ-IFN.CAT is arranged as depicted in FIG. 4D, where "TCR" represents the γ-IFN transcriptional control region, "Gene" represents the CAT gene and "ENH" represents the CMV enhancer. HyTK.CMVe.γ-IFN.CAT was constructed using standard techniques (Ausubel et al., 1987) as follows: Plasmid tgγ-IFNcat was constructed first. This plasmid contains nucleotides −541 to +128 of the human γ-IFN transcriptional control region (Ciccarone et al., 1990; Gray and Goeddel, 1982) linked to the CAT gene followed by a retroviral LTR sequence to provide a polyadenylation signal, and contains an XhoI site 5' of the γ-IFN transcriptional control region. A fragment spanning the HCMV IE94 enhancer was excised from HyTK.CMVe.CTLA-1.CAT (see Example 15) using XhoI and HindIII, and T4 DNA polymerase was used to render the HindIII cohesive end blunt. This fragment was then ligated into the XhoI site of tgγ-IFNcat after T4 DNA polymerase was used to render one of the XhoI cohesive ends blunt, to create tgCMVe.γ-IFNcat. The orientation of the enhancer was confirmed by restriction enzyme digestion. A fragment spanning the CMV enhancer, the γ-IFN transcriptional control region, and the 5' end of the CAT gene was then excised using XhoI and EcoRI and ligated between XhoI and EcoRI sites of HyTK.CMV.CAT (see Example 10) to create HyTK.CMVe.γ-IFN.CAT.

To derive stable PA317 cell lines producing amphotropic HyTK.CMV.CAT or HyTK.CMVe.γ-IFN.CAT viral particles, the retroviral plasmid DNAs were first transfected into ψ2 ecotropic packaging cells. ψ2 cells (Mann et al., 1983) were grown in DMEM supplemented with 10% bovine calf serum, 2 mM L-glutamine, 50 U/ml penicillin, and 50 µg/ml streptomycin at 37° C. in a humidified atmosphere supplemented with 10% $CO_2$. For transfection, exponentially growing cells were harvested by trypsinization, washed free of serum, and resuspended in DMEM at a concentration of $10^7$ cells/ml. Plasmid DNA (5–20 µg) was added to 800 µl of cell suspension (8×$10^6$ cells), and the mixture subjected to electroporation using the Biorad Gene Pulser and Capacitance Extender (200–300 V, 960 µF, 0.4 cm electrode gap, at ambient temperature). The transfected ψ2 cells were then transferred to a 10-cm tissue culture dish containing 10 ml of complete growth medium supplemented with 10 mM sodium butyrate, and allowed to attach overnight. After 15 h, the medium was removed and replaced with fresh medium. After a further 24 h, the medium containing transiently produced amphotropic virus particles was harvested, centrifuged at 2000 rpm for 10 min, and used to infect PA317 amphotropic packaging cells (Miller and Buttimore, 1986). PA317 cells were grown in DMEM supplemented with 10% fetal bovine serum, 2 mM L-glutamine, 50 U/ml penicillin, and 50 µg/ml streptomycin at 37° C. in a humidified atmosphere supplemented with 10% $CO_2$. Exponentially dividing PA317 cells were plated at a density of $10^6$ cells/10-cm tissue culture dish, and allowed to attach overnight. The following day, the medium was removed and replaced with serial dilutions of the virus-containing supernatant (6 ml/dish) in medium supplemented with 4 µg/ml polybrene. Infection was allowed to proceed overnight, and then the supernatant was replaced with complete growth medium. Infected cells were selected for drug resistance after a further 8–24 h of growth by adding hygromycin B to a final concentration of 500 µg/ml. Colonies of $Hm^r$ cells were isolated using cloning cylinders 12–14 days later and individually expanded or were pooled and expanded as polyclonal cultures. The cells were subjected to Southern analysis to determine the integrity of the retroviral provirus, and the production of retroviral particles was measured by titering on NIH 3T3 cells using standard techniques (Ausubel et al., 1987). Cultures that contained an unrearranged retroviral provirus and produced a high titer of infectious retrovirus particles were used to infect human Jurkat T lymphocytes.

Jurkat cells were grown in RPMI 1640 medium supplemented with 10% fetal bovine serum, 0.1 mM non-essential amino acids, 50 μM 2-mercaptoethanol, 2 mM L-glutamine, 50 U/ml penicillin, and 50 μg/ml streptomycin at 37° C. in a humidified atmosphere supplemented with 5% $CO_2$. Aliquots ($5 \times 10^6$) of cells were incubated with 5 ml of supernatant from the amphotropic PA317 retrovirus producer cells supplemented with 4 μg/ml of polybrene for 24 h. The cells were then collected by centrifuging at 1600 RPM for 10 min at 4° C. in a Sorvall RT6000D benchtop centrifuge and resuspended in 20 ml of complete medium. After incubation for 24 h, the cells were plated in 96 well trays at densities of 50, 10, 1 or 0.1 cell/well in a volume of 0.2 ml/well of complete medium. After incubation for 7 d, 0.1 ml of medium was removed from each well and replaced with 0.1 ml of complete medium supplemented with 400 μg/ml of Hygromycin B. After a further 7–14 d of incubation, $Hm^r$ clones of cells were transferred to 24 well trays and expanded for analysis.

For the preparation and assay of CAT extracts, aliquots ($4 \times 10^6$) of the infected cells were either left unactivated, or were activated by cross-linking the T cell receptor with a surface-bound anti-CD3 monoclonal antibody. At 24 h after activation, the cells were harvested and CAT extracts were prepared and assayed as described in Example 12, except that extracts were prepared in 60 μl of 0.25M Tris (pH 8.0).

Figure 13:
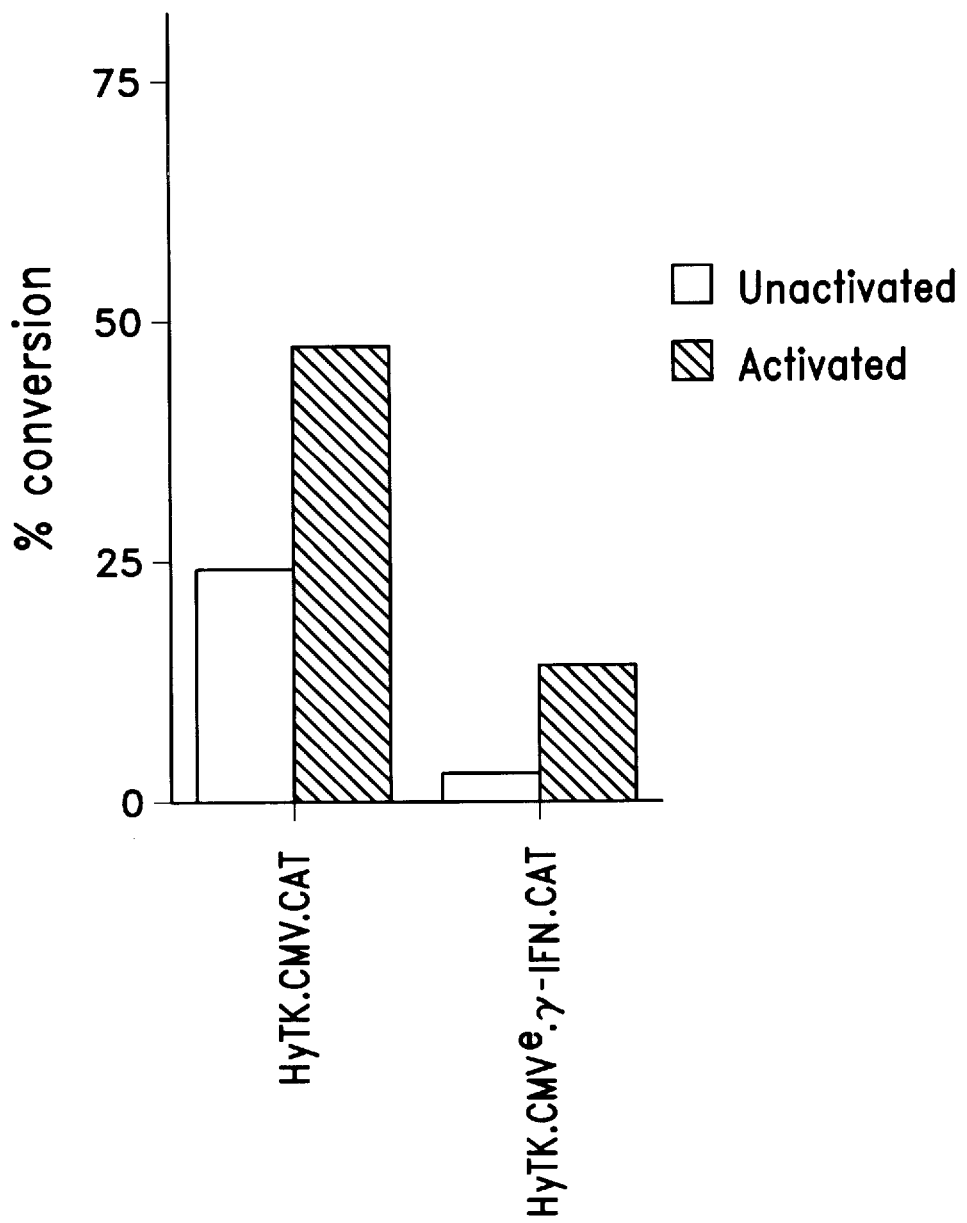
FIG. 13 is a bar graph depicting the level of CAT activity expressed by human Jurkat T lymphocytes transfected with the vectors listed, with or without activation of the cells by cross-linking the T cell receptor using a surface-bound anti-CD3 monoclonal antibody, as described in Example 17.

As shown in FIG. 13, cells infected with the positive control retroviral vector, HyTK.CMV.CAT and left unactivated constitutively expressed CAT activity and the level of expression was increased upon T cell activation. Cells infected with the HyTK.CMVe.γ-IFN.CAT retroviral vector and left unactivated, did not express significant levels of CAT activity. However, cells infected with the HyTK.CMVe.γ-IFN.CAT retroviral vector expressed significant levels of CAT activity following activation for 24 h.

The results demonstrate that the γ-IFN transcriptional control region in combination with the CMV enhancer mediates activation-induced expression in human T lymphocytes. The results further demonstrate that the γ-IFN transcriptional control region in combination with the CMV enhancer is functional in human T lymphocytes when inserted into a retroviral vector and delivered via retroviral infection.

EXAMPLE 18

Activation-induced expression mediated by the γ-IFN transcriptional control region in combination with the CMV enhancer and the IL-3 transcriptional control region in combination with the CMV enhancer in human peripheral blood T lymphocytes Plasmids HyTK.lck-7.CAT and HyTK.CMV.CAT were prepared as in Example 10. Plasmids HyTK.hIL-3.CAT and HyTK.CMVe.hIL-3.CAT were constructed as described in Example 4 and Example 14. Plasmid HyTK.CMVe.γ-IFN.CAT was constructed as described in Example 17.

The proviral structure of retroviral vector HyTK.γ-IFN.CAT is arranged as depicted in FIG. 4C, where "TCR" represents the γ-IFN transcriptional control region, and "Gene" represents the CAT gene. HyTK.γ-IFN.CAT was constructed using standard techniques (Ausubel et al., 1987) as follows: An XhoI-EcoRI fragment spanning the γ-IFN transcriptional control region and the 5' end of the CAT gene was excised from tgγ-IFNcat (see Example 17), and a BstE2-XhoI fragment spanning the HyTK gene was excised from HyTK.CMV.IL-2 (see Example 10). These two fragments were then ligated between the BstE2 and EcoRI sites of HyTK.CMV.CAT (see Example 10) to create HyTK.γ-IFN.CAT.

Human peripheral blood T cells were prepared and transfected as described in Example 12, except that the cells were transfected with 50 μg of HyTK.lck-7.CAT, HyTK.CMV.CAT, HyTK.γ-IFN.CAT, HyTK.CMVe.γ-IFN.CAT, HyTK.IL-3.CAT, or HyTK.CMVe.IL-3.CAT plasmid DNA.

The transfected cells were either left unactivated (−), or were activated by cross-linking the T cell receptor with a surface-bound anti-CD3 monoclonal antibody immediately following transfection (+). At 20 h after activation, the cells were harvested and CAT extracts were prepared and assayed as described in Example 12, except that a 5 μl aliquot of extract prepared from cells transfected with HyTK.CMV.CAT was assayed.

Figure 14:
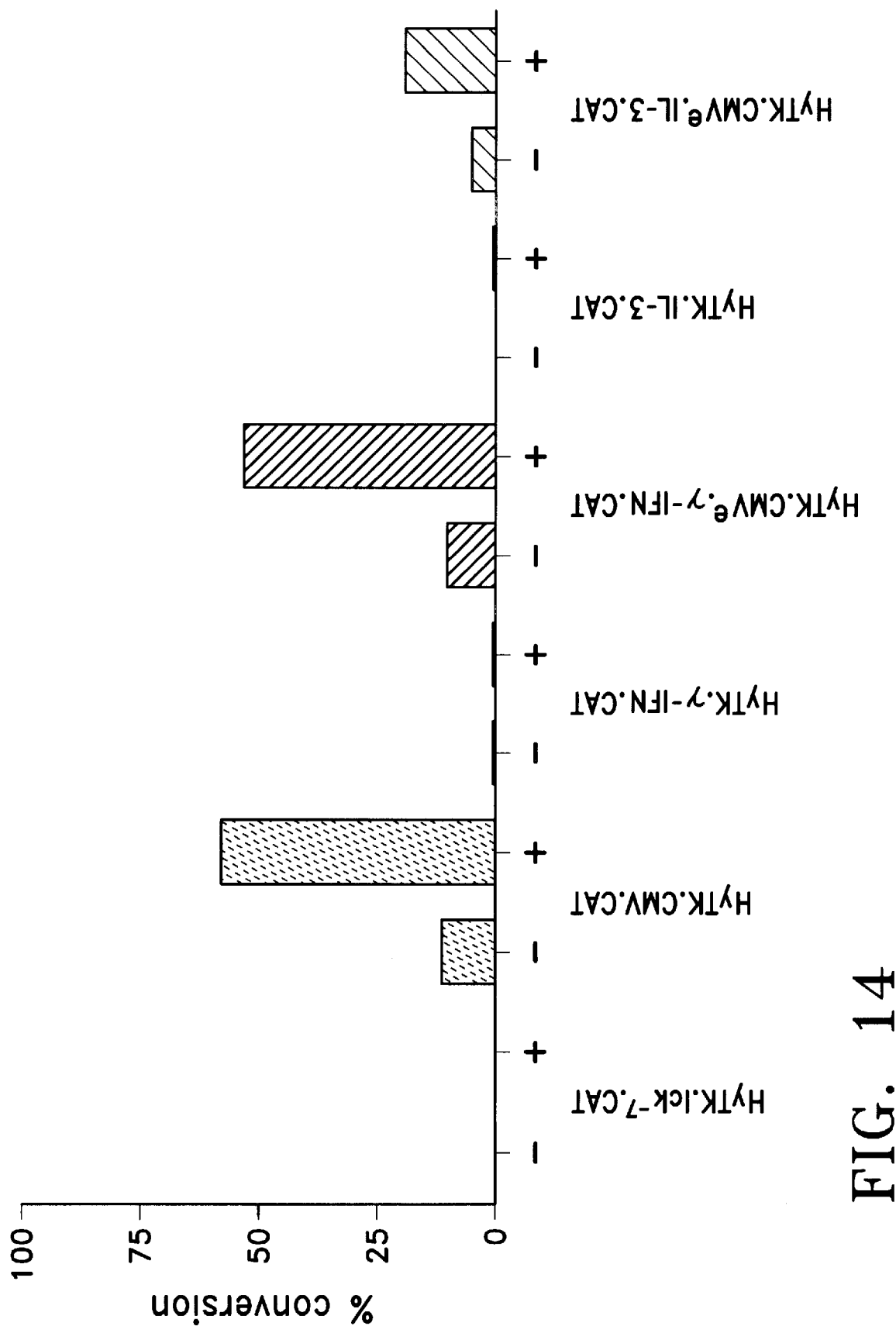
FIG. 14 is a bar graph depicting the level of CAT activity expressed by human peripheral T lymphocytes transfected with the vectors listed, with (+) or without (-) activation of the cells by cross-linking the T cell receptor with a surface-bound anti-CD3, as described in Example 18.

As shown in FIG. 14, cells transfected with the negative control vector, HyTK.lck-7.CAT, and left unactivated (−) or activated (+) did not express significant levels of CAT activity. Cells transfected with the positive control vector, HyTK.CMV.CAT, and left unactivated (−) constitutively expressed CAT activity and the level of expression was increased upon T cell activation (+). Cells transfected with HyTK.CMVe.γ-IFN.CAT or HyTK.CMVe.IL-3.CAT and left unactivated (−), did not express significant levels of CAT activity. However, cells transfected with HyTK.CMVe.γ-IFN.CAT or HyTK.CMVe.IL-3.CAT expressed significant levels of CAT activity following activation for 20 h (+).

The results demonstrate that the γ-IFN transcriptional control region in combination with the CMV enhancer and the IL-3 transcriptional control region in combination with the CMV enhancer mediate activation-induced expression in human T lymphocytes, and that the CMV enhancer may be used to enhance the level of activation-induced expression from the γ-IFN and IL-3 transcriptional control regions in human T lymphocytes. The results further demonstrate that the γ-IFN transcriptional control region in combination with the CMV enhancer and the IL-3 transcriptional control region in combination with the CMV enhancer are functional in human T lymphocytes when inserted into a retroviral vector.

EXAMPLE 19

Activation-induced expression in murine T lymphocytes

Plasmids HyTK.lck-7.CAT, HyTK.CMV.CAT and HyTK.CMVe.LT.CAT were constructed as described in Example 10. Plasmids HyTK.CMVe.IL-2Rα.CAT, HyTK.CMVe.hIL-3.CAT, HyTK.CMVe.CTLA-1.CAT and HyTK.CMVe.γ-IFN.CAT were constructed as described in Examples 11, 14, 15 and 17, respectively.

Preparation and transfection of murine T lymphocytes was carried out as follows. Spleens were removed from C57Bl/6 mice and DBA/2 mice and disaggregated in complete medium (Iscove's medium supplemented with 10% fetal bovine serum, 0.1 mM non-essential amino acids, 50 μM 2-mercaptoethanol, 2 mM L-glutamine, 1 mM sodium pyruvate, 50 U/ml penicillin, and 50 μg/ml streptomycin) to form single cell suspensions. The cells were then layered over isolymph in a 50 ml conical tube and centrifuged at 2000 RPM for 20 min at 20° C. in a Sorvall RT6000D benchtop centrifuge. The cells at the interface were pelleted by centrifuging at 1600 RPM for 10 min at 4° C. in a Sorvall RT6000D benchtop centrifuge, washed two times by resuspending in complete medium and centrifuging at 1600 RPM for 10 min at 4° C. in a Sorvall RT6000D benchtop centrifuge and resuspending in complete medium. The DBA/2 cells were then irradiated with 3500 rads, and a mixed leukocyte culture (MLC) was initiated by mixing $7.5 \times 10^7$ irradiated DBA/2 cells with $7.5 \times 10^7$ C57Bl/6 cells in a volume of 20 ml in a T-75 culture flask. After incubation at 37° C. in a humidified atmosphere supplemented with 5% $CO_2$ for 3 d, the cells were harvested from the MLC, pelleted by centrifuging at 1600 RPM for 10 min at 4° C. in a Sorvall RT6000D benchtop centrifuge, and then resuspended in 30 ml of complete medium. The cells were then layered over isolymph in a 50 ml conical tube and centrifuged at 2000 RPM for 20 min at 20° C. in a Sorvall RT6000D benchtop centrifuge. The cells at the interface were pelleted by centrifuging at 1600 RPM for 10 min at 4° C. in a Sorvall RT6000D benchtop centrifuge, washed two times by resuspending in complete medium and centrifuging at 1600 RPM for 10 min at 4° C. in a Sorvall RT6000D benchtop centrifuge, and then $7.5 \times 10^6$ cells were resuspended in 30 ml of complete medium supplemented with 5 ng/ml of recombinant human IL-2 in a T-75 flask. After a further 3 d of incubation at 37° C. in a humidified atmosphere supplemented with 5% $CO_2$, the T cells were purified by affinity chromatography using a CD3+ T cell purification column (Biotecx) using standard procedures. Aliquots of cells ($1 \times 10^7$ were electroporated with 50 μg of HyTK.lck-7.CAT, HyTK.CMV.CAT, HyTK.CMVe.γ-IFN.CAT, HyTK.CMVe.hIL-3.CAT, HyTK.CMVe.LT.CAT, HyTK.CMVe.CTLA-1.CAT, HyTK.CMVe.IL-2Rα.CAT plasmid DNA in 0.8 ml of complete medium using a 0.4 cm cuvette and a Biorad Gene Pulser set at 300 V and 960 μF.

For preparation and assay of CAT extracts, the transfected cells were either left unactivated or were activated by cross-linking the T cell receptor with a surface-bound anti-CD3 monoclonal antibody immediately following transfection. At 24 h after activation, the cells were harvested and CAT extracts were prepared and assayed as described in Example 12, except that extracts were prepared in 60 μl of 0.25M Tris (pH 8.0) and a 5 μl aliquot of extract prepared from cells transfected with HyTK.CMV.CAT was assayed.

Figure 15:
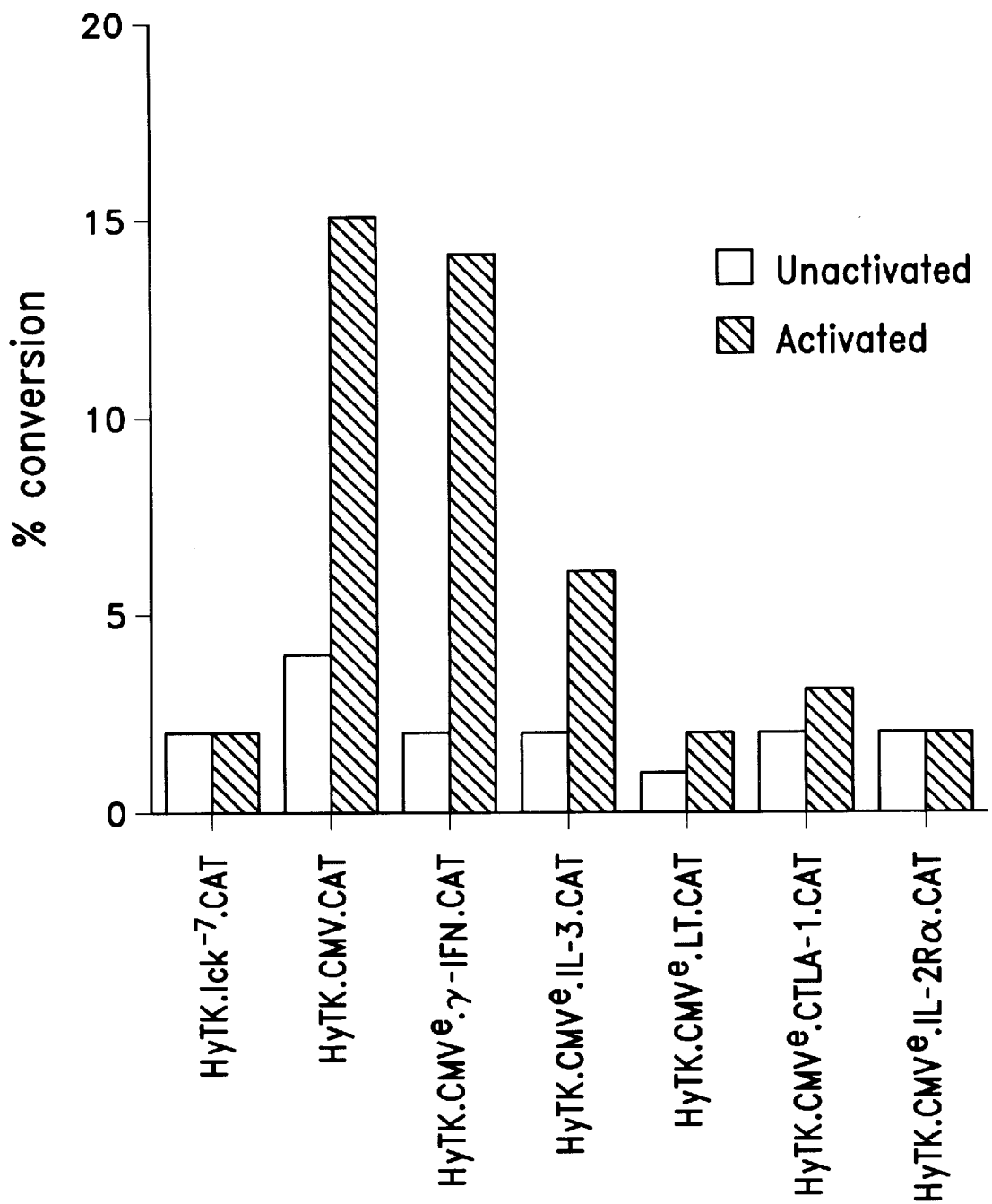
FIG. 15 is a bar graph depicting the level of CAT activity expressed by mouse CD3+ splenocytes transfected with the vectors listed, with or without activation of the cells by cross-linking the T cell receptor using anti-CD3 antibody, as described in Example 19.

As shown in FIG. 15, cells transfected with the negative control vector HyTK.lck-7.CAT, and either left unactivated or activated did not express significant levels of CAT activity. Cells transfected with the positive control vector, HyTK.CMV.CAT and left unactivated constitutively expressed CAT activity and the level of expression was increased upon T cell activation. Cells transfected with HyTK.CMVe.γ-IFN.CAT or HyTK.CMVe.IL-3.CAT and left unactivated did not express significant levels of CAT activity. However, cells transfected with HyTK.CMVe.γ-IFN.CAT or HyTK.CMVe.IL-3.CAT expressed significant levels of CAT activity following activation for 24 h. A small amount of activation induced expression was also seen in cells transfected with HyTK.CMVe.LT.CAT or HyTK.CMVe.CTLA-1.CAT.

The results demonstrate that the γ-IFN transcriptional control region in combination with the CMV enhancer and the IL-3 transcriptional control region in combination with the CMV enhancer mediate activation-induced expression in murine T lymphocytes. The results further demonstrate that the γ-IFN transcriptional control region in combination with the CMV enhancer and the IL-3 transcriptional control region in combination with the CMV enhancer are functional in murine T lymphocytes when inserted into a retroviral vector.

EXAMPLE 20

Antigen-induced expression mediated by the γ-IFN transcriptional control region in combination with the CMV enhancer in murine T lymphocytes Plasmid constructions:

Plasmids HyTK.lck-7.CAT and HyTK.CMV.CAT were constructed as in Example 10. Plasmid HyTK.CMVe.γ-IFN.CAT was constructed as in Example 17.

Preparation and transfection of murine T lymphocytes was carried out as described in Example 19.

For preparation and assay of CAT extracts, the transfected cells were either left unactivated by incubating in the presence of irradiated C57Bl/6 splenocytes, or were activated immediately following transfection by incubating in the presence of irradiated allogeneic DBA/2 splenocytes to provide an antigenic stimulus. At 24 h after activation, the cells were harvested and CAT extracts were prepared and assayed as described in Example 19.

Figure 16:
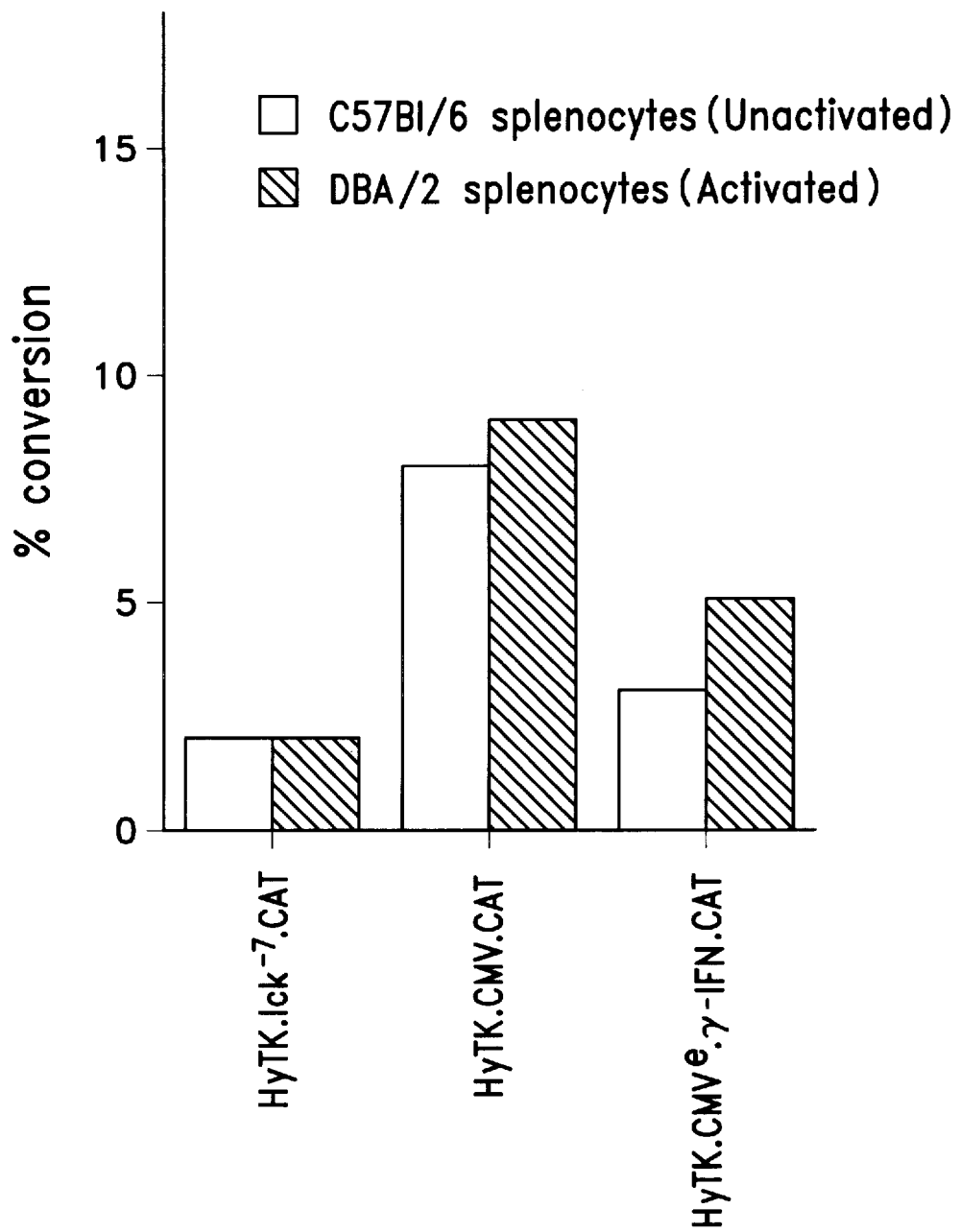
FIG. 16 is a bar graph depicting the level of CAT activity expressed by mouse CD3+ splenocytes transfected with the vectors listed, either unactivated by incubating with irradiated C57Bl/6 splenocytes, or activated by incubating with irradiated allogeneic DBA/2 splenocytes, as described in Example 20.

As shown in FIG. 16, cells transfected with the negative control vector, HyTK.lck-7.CAT, and left unactivated or activated with antigen did not express significant levels of CAT activity. Cells transfected with the positive control vector, HyTK.CMV.CAT, and left unactivated constitutively expressed CAT activity and the level of expression was increased upon antigen activation. Cells transfected with HyTK.CMVe.γ-IFN.CAT and left unactivated, did not express significant levels of CAT activity. However, cells transfected with HyTK.CMVe.γ-IFN.CAT expressed significant levels of CAT activity following activation for 24 b with antigen.

The results demonstrate that the γ-IFN transcriptional control region in combination with the CMV enhancer mediates antigen-induced expression in murine T lymphocytes. The results further demonstrate that the γ-IFN transcriptional control region in combination with the CMV enhancer is functional in murine T lymphocytes when inserted into a retroviral vector.

EXAMPLE 21

Activation-induced expression in CD8+murine T lymphocytes

Plasmid constructions:

Plasmids HyTK.lck-7.CAT, HyTK.CMV.CAT and HyTK.CMVe.LT.CAT were constructed as in Example 10. Plasmids HyTK.CMVe.IL-2Rα.CAT, HyTK.CMVe.hIL-3.CAT, HyTK.CMVe.CTLA-1.CAT and HyTK.CMVe.γ-IFN.CAT were constructed as described in Examples 11, 14, 15 and 17, respectively.

For preparation and transfection of CD8+ murine T lymphocytes, CD8+ T lymphocytes were prepared and transfected as described in Example 19, except that the CD8+ cells were purified using a CD8+T cell purification column instead of a CD3+ T cell purification column.

Preparation and assay of CAT extracts was carried out as described in Example 19.

Figure 17:
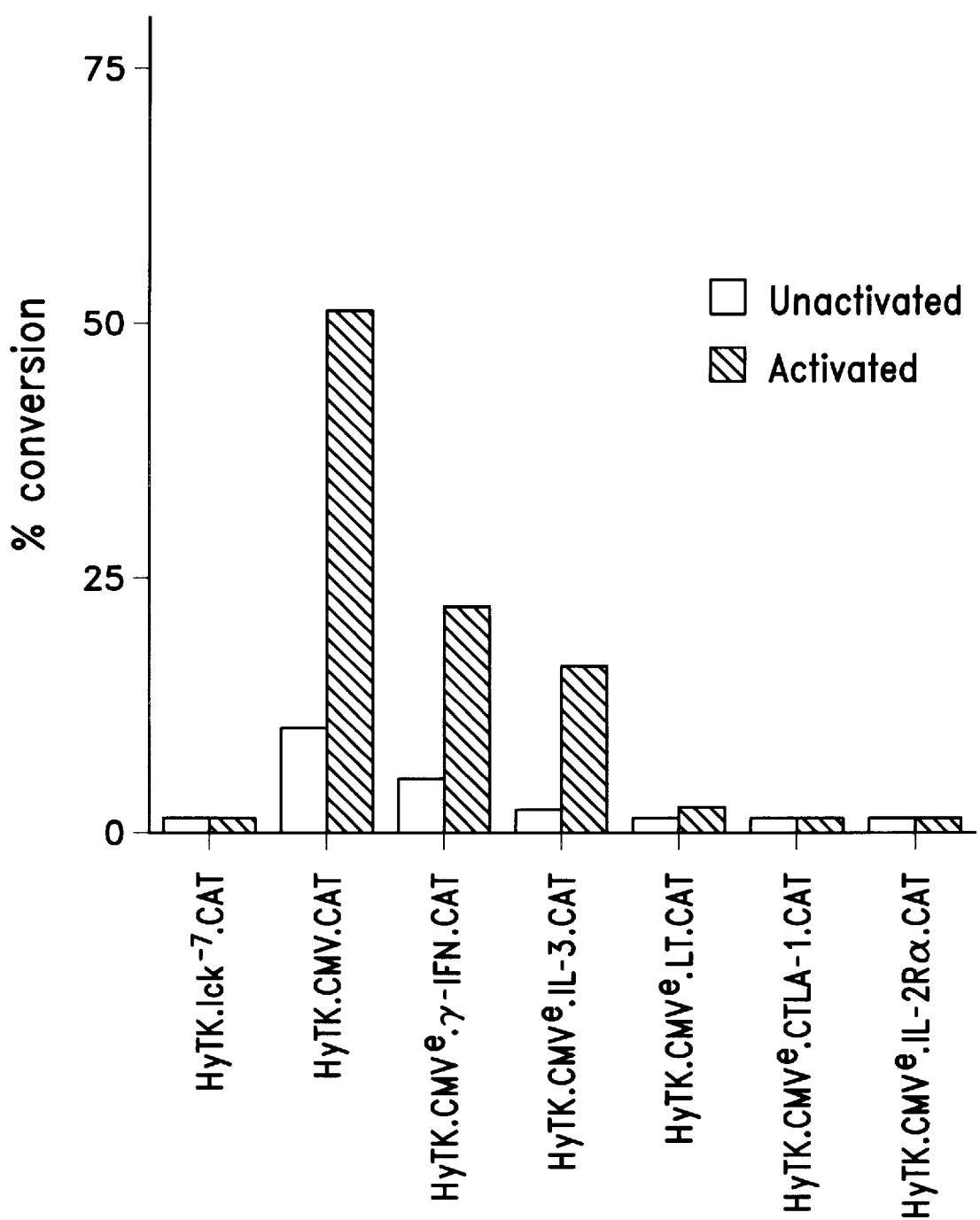
FIG. 17 is a bar graph depicting the level of expression of CAT activity by mouse CD8+ T cells transfected with the vectors listed, with or without activation, as described in Example 21.

As shown in FIG. 17, cells transfected with the negative control vector HyTK.lck-7.CAT, and either left unactivated or activated did not express significant levels of CAT activity. Cells transfected with the positive control vector, HyTK.CMV.CAT and left unactivated constitutively expressed CAT activity and the level of expression was increased upon T cell activation. Cells transfected with HyTK.CMVe.γ-IFN.CAT or HyTK.CMVe.IL-3.CAT and left unactivated did not express significant levels of CAT activity. However, cells transfected with HyTK.CMVe.γ-IFN.CAT or HyTK.CMVe.IL-3.CAT expressed significant levels of CAT activity following activation for 24 h. A small amount of activation-induced expression was also seen in cells transfected with HyTK.CMVe.LT.CAT.

The results demonstrate that the γ-IFN transcriptional control region in combination with the CMV enhancer and the IL-3 transcriptional control region in combination with the CMV enhancer mediate activation-induced expression in murine CD8+ T lymphocytes. The results further demonstrate that the γ-IFN transcriptional control region in combination with the CMV enhancer and the IL-3 transcriptional control region in combination with the CMV enhancer are functional in murine CD8+ T lymphocytes when inserted into a retroviral vector.

EXAMPLE 22

Antigen-induced expression mediated by the γ-IFN transcriptional control region in combination with the CMV enhancer in CD8+ murine T lymphocytes
Plasmid constructions:

Plasmids HyTK.lck-7.CAT and HyTK.CMV.CAT were constructed as in Example 10. Plasmid HyTK.CMVe.γ-IFN.CAT was constructed as in Example 17.

Preparation and transfection of murine T lymphocytes was carried out as described in Example 21.

For preparation and assay of CAT extracts, the transfected cells were either left unactivated by incubating in the presence of irradiated C57Bl/6 splenocytes, or were activated immediately following transfection by incubating in the presence of irradiated allogeneic DBA/2 splenocytes to provide an antigenic stimulus. At 24 h after activation, the cells were harvested and CAT extracts were prepared and assayed as described in Example 19.

Figure 18:
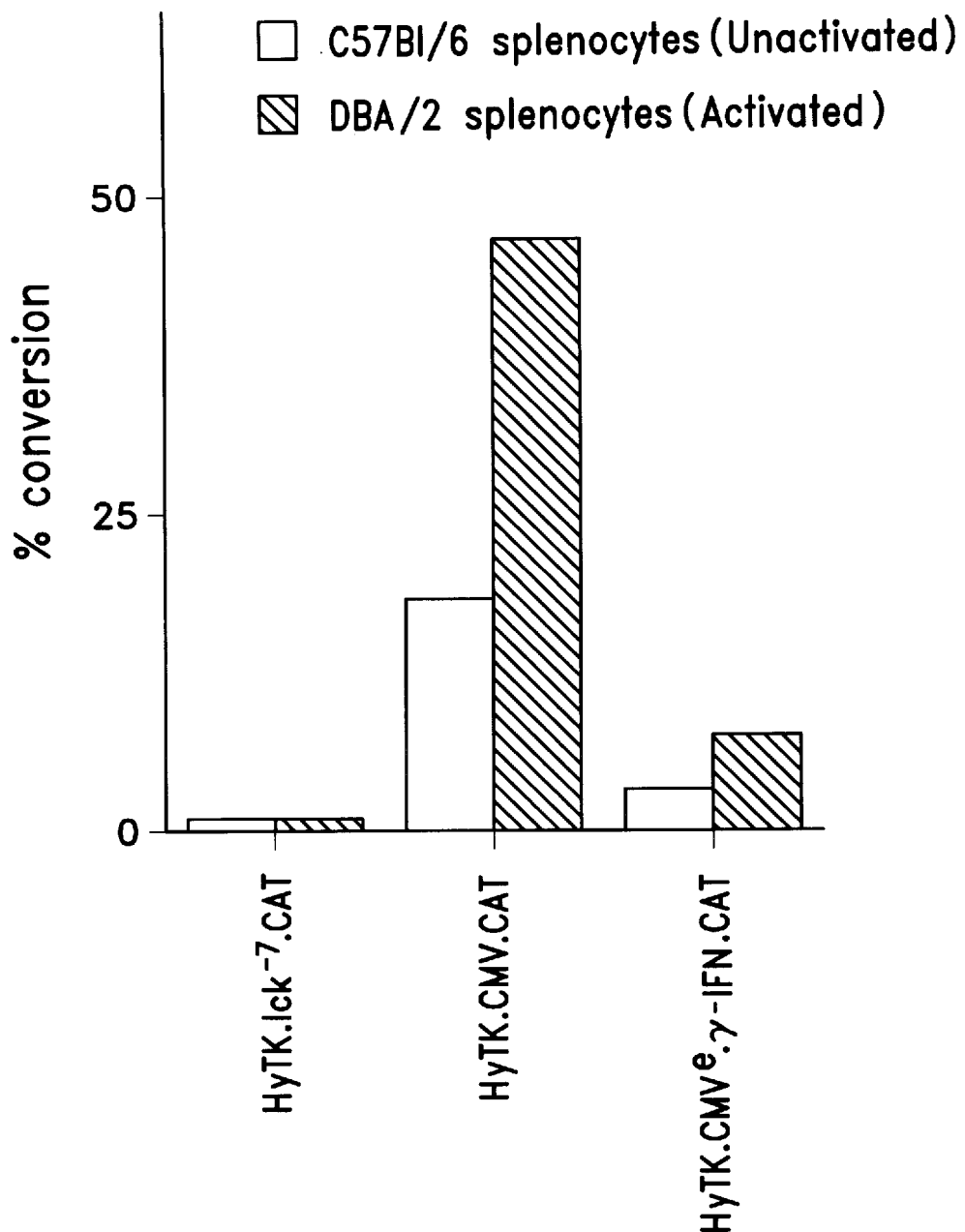
FIG. 18 is a bar graph depicting the level of CAT activity expressed by mouse CD8+ T cells transfected with the vectors listed, either unactivated by incubating with irradiated C57Bl/6 splenocytes, or activated by incubating with irradiated allogeneic DBA/2 splenocytes, as described in Example 22.

As shown in FIG. 18, cells transfected with the negative control vector, HyTK.lck-7.CAT, and left unactivated or activated with antigen did not express significant levels of CAT activity. Cells transfected with the positive control vector, HyTK.CMV.CAT, and left unactivated constitutively expressed CAT activity and the level of expression was increased upon antigen activation. Cells transfected with HyTK.CMVe.γ-IFN.CAT and left unactivated, did not express significant levels of CAT activity. However, cells transfected with HyTK.CMVe.γ-IFN.CAT expressed significant levels of CAT activity following activation for 24 h with antigen.

The results demonstrate that the γ-IFN transcriptional control region in combination with the CMV enhancer mediates antigen-induced expression in murine CDB+ T lymphocytes. The results further demonstrate that the γ-IFN transcriptional control region in combination with the CMV enhancer is functional in murine CD8+ T lymphocytes when inserted into a retroviral vector.

EXAMPLE 23

Activation-induced expression in human peripheral blood T lymphocytes
Plasmid constructions:

Plasmids HyTK.lck-7.CAT, HyTK.CMV.CAT and HyTK.CMVe.LT.CAT were constructed as in Example 10. Plasmids HyTK.CMVe.IL-2Rα.CAT, HyTK.CMVe.hIL-3.CAT, HyTK.CMVe.CTLA-1.CAT and HyTK.CMVe.γ-IFN.CAT were constructed as described in Examples 11, 14, 15 and 17, respectively.

Human peripheral blood T cells were prepared and transfected as described in Example 12, except that the cells were transfected with 100 μg of HyTK.lck-7.CAT, HyTK.CMV.CAT, HyTK.γ-IFN.CAT, HyTK.CMVe.γ-IFN.CAT, HyTK.IL-3.CAT, or HyTK.CMVe.IL-3.CAT plasmid DNA using a 0.4 cm cuvette and a Biorad Gene Pulser set at 400 V and 960 μF.

For preparation and assay of CAT extracts, the transfected cells were either left unactivated, or were activated by cross-linking the T cell receptor with a surface-bound anti-CD3 monoclonal antibody immediately following transfection. At 24 h after activation, the cells were harvested and CAT extracts were prepared and assayed as described in Example 12, except that extracts were prepared in 60 μl of 0.25M Tris (pH 8.0) and a 5 μl aliquot of extract prepared from cells transfected with HyTK.CMV.CAT was assayed.

Figure 19:
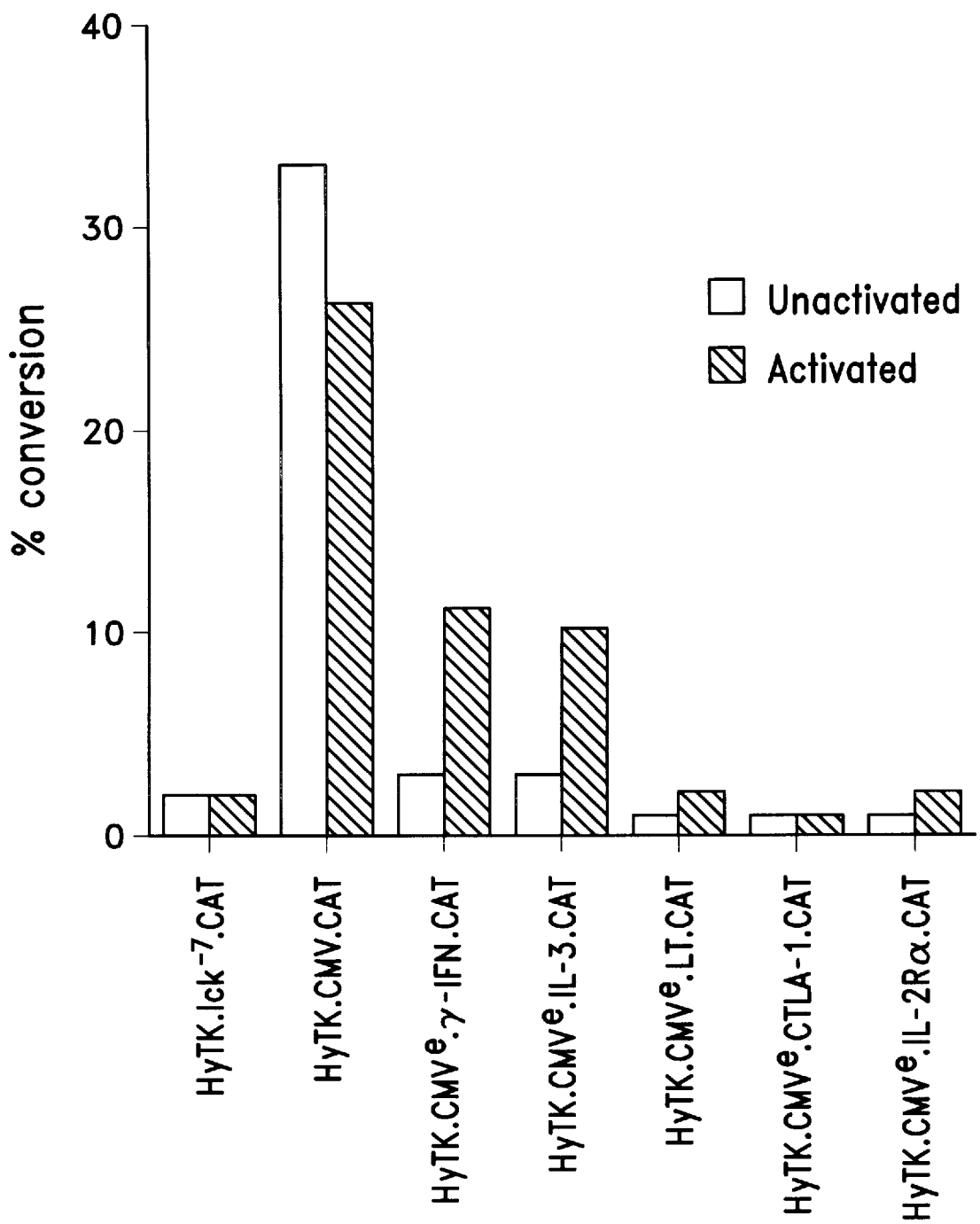
FIG. 19 is a bar graph depicting the level of CAT activity expressed by human peripheral T lymphocytes transfected with the vectors listed, with or without activation of the cells by cross-linking the T cell receptor using anti-CD3 antibody, as described in Example 23.

As shown in FIG. 19, cells transfected with the negative control vector, HyTK.lck-7.CAT, and either left unactivated or activated did not express significant levels of CAT activity. Cells transfected with the positive control vector, HyTK.CMV.CAT, and left unactivated constitutively expressed CAT activity and the level of expression was reduced upon T cell activation. Cells transfected with HyTK.CMVe.γ-IFN.CAT or HyTK.CMVe.IL-3.CAT and left unactivated, did not express significant levels of CAT activity. However, cells transfected with HyTK.CMVe.γ-IFN.CAT or HyTK.CMVe.IL-3.CAT expressed significant levels of CAT activity following activation for 24 h. A small amount of activation-induced expression was also seen in cells transfected with HyTK.CMVe.LT.CAT or HyTK.CMVe.IL-2Rα.CAT.

The results demonstrate that the γ-IFN transcriptional control region in combination with the CMV enhancer and the IL-3 transcriptional control region in combination with the CMV enhancer mediate activation-induced expression in human T lymphocytes. The results further demonstrate the γ-IFN transcriptional control region in combination with the CMV enhancer and the IL-3 transcriptional control region in combination with the CMV enhancer are functional in human T lymphocytes when inserted into a retroviral vector.

EXAMPLE 24

Activation-induced expression in CD4+ human peripheral blood T lymphocytes
Plasmid constructions:

Plasmids HyTK.lck-7. CAT, HyTK.CMV.CAT and HyTK.CMVe.LT.CAT were constructed as in Example 10. Plasmids HyTK.CMVe.IL-2Rα.CAT, HyTK.CMVe.hIL-3.CAT, HyTK.CMVe.CTLA-1.CAT and HyTK.CMVe.γ-IFN.CAT were constructed as described in Examples 11, 14, 15 and 17, respectively.

Human peripheral blood T cells were prepared as described in Example 12. The CD8+ cells were then removed from the population by using CD8-conjugated magnetic beads (Dynal). Aliquots (4×10$^6$) of the purified cells were transfected with 100 μg of HyTK.lck-7.CAT, HyTK.CMV.CAT, HyTK.γ-IFN.CAT, HyTK.CMVe.γ-IFN.CAT, HyTK.IL-3.CAT, or HyTK.CMVe.IL-3.CAT plasmid DNA in 0.8 ml of complete medium in a 0.4 cm cuvette using a Biorad Gene Pulser set at 400 V and 960 μF.

The preparation and assay of CAT extracts was carried out as described in Example 23.

Figure 20:
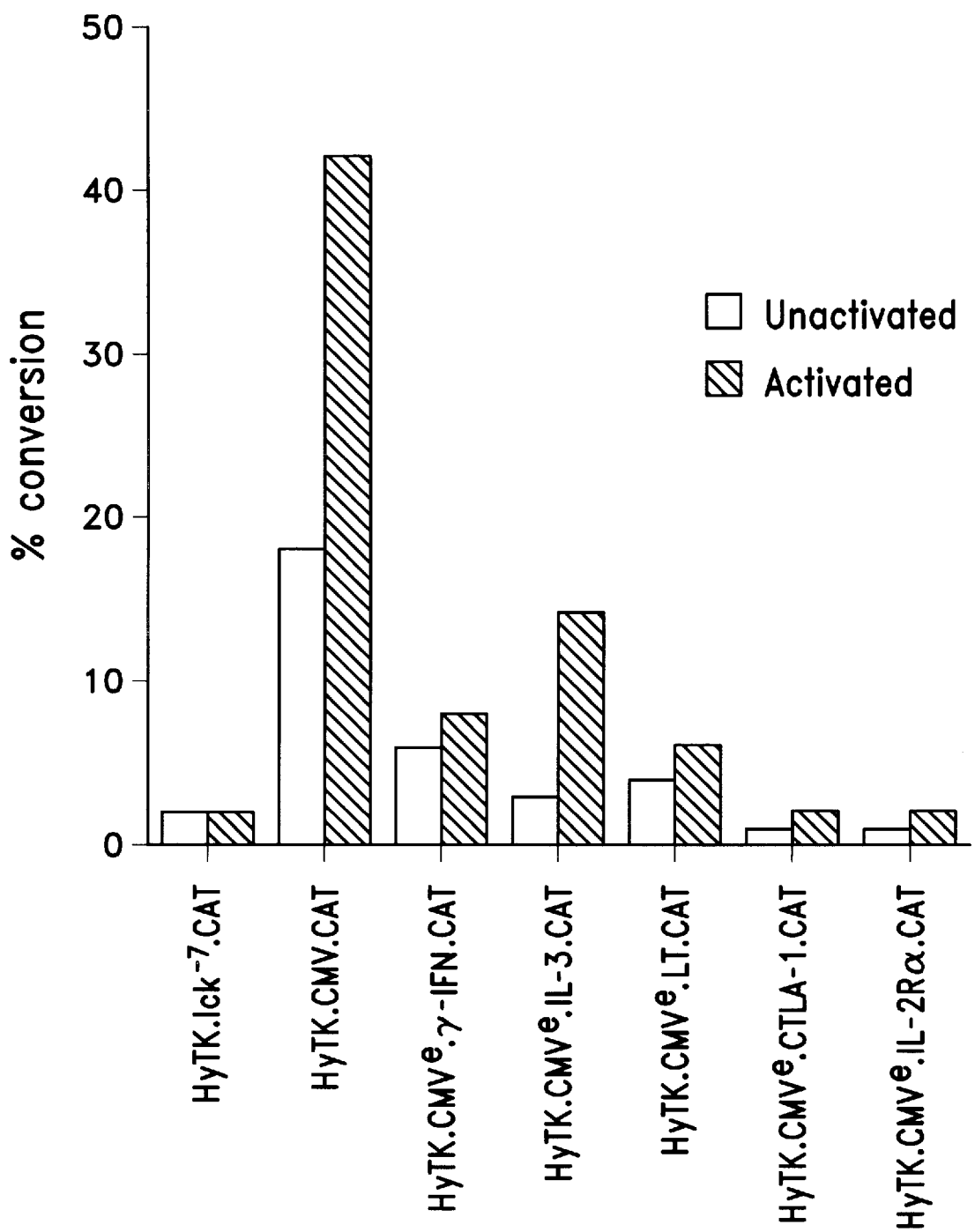
FIG. 20 is a bar graph depicting the level of CAT activity expressed by CD4+ human peripheral T lymphocytes transfected with the vectors listed, with or without activation of the cells, as described in Example 24.

As shown in FIG. 20, cells transfected with the negative control vector, HyTK.lck-7.CAT, and either left unactivated or activated did not express significant levels of CAT activity. Cells transfected with the positive control vector, HyTK.CMV.CAT, and left unactivated constitutively expressed CAT activity and the level of expression was increased upon T cell activation. Cells transfected with HyTK.CMVe.IL-3.CAT and left unactivated, did not express significant levels of CAT activity. However, cells transfected with HyTK.CMVe.IL-3.CAT expressed significant levels of CAT activity following activation for 24 h. Lower levels of activation-induced expression were also seen in cells transfected with HyTK.CMVe.γ-IFN.CAT, or HyTK.CMVe.LT.CAT, HyTK.CMVe.CTLA-1.CAT or HyTK.CMVe.IL-2Rα.CAT.

The results demonstrate that the IL-3 transcriptional control region in combination with the CMV enhancer mediates activation-induced expression in human CD4+ T lymphocytes. The results further demonstrate that the IL-3 transcriptional control region in combination with the CMV enhancer is functional in human CD4+ T lymphocytes when inserted into a retroviral vector.

EXAMPLE 25
Activation-induced expression in CD8+ human peripheral blood T lymphocytes
Plasmid constructions:

Plasmids HyTK.lck-7.CAT, HyTK.CMV.CAT and HyTK.CMVe.LT.CAT were constructed as in Example 10. Plasmids HyTK.CMVe.IL-2Rα.CAT, HyTK.CMVe.hIL-3.CAT, HyTK.CMVe.CTLA-1.CAT and HyTK.CMVe.γ-IFN.CAT were constructed as described in Examples 11, 14, 15 and 17, respectively.

Human peripheral blood T cells were prepared as described in Example 24, except that the CD4+ cells were then removed from the population by using CD4-conjugated magnetic beads (Dynal).

The preparation and assay of CAT extracts was carried out as described in Example 23.

Figure 21:
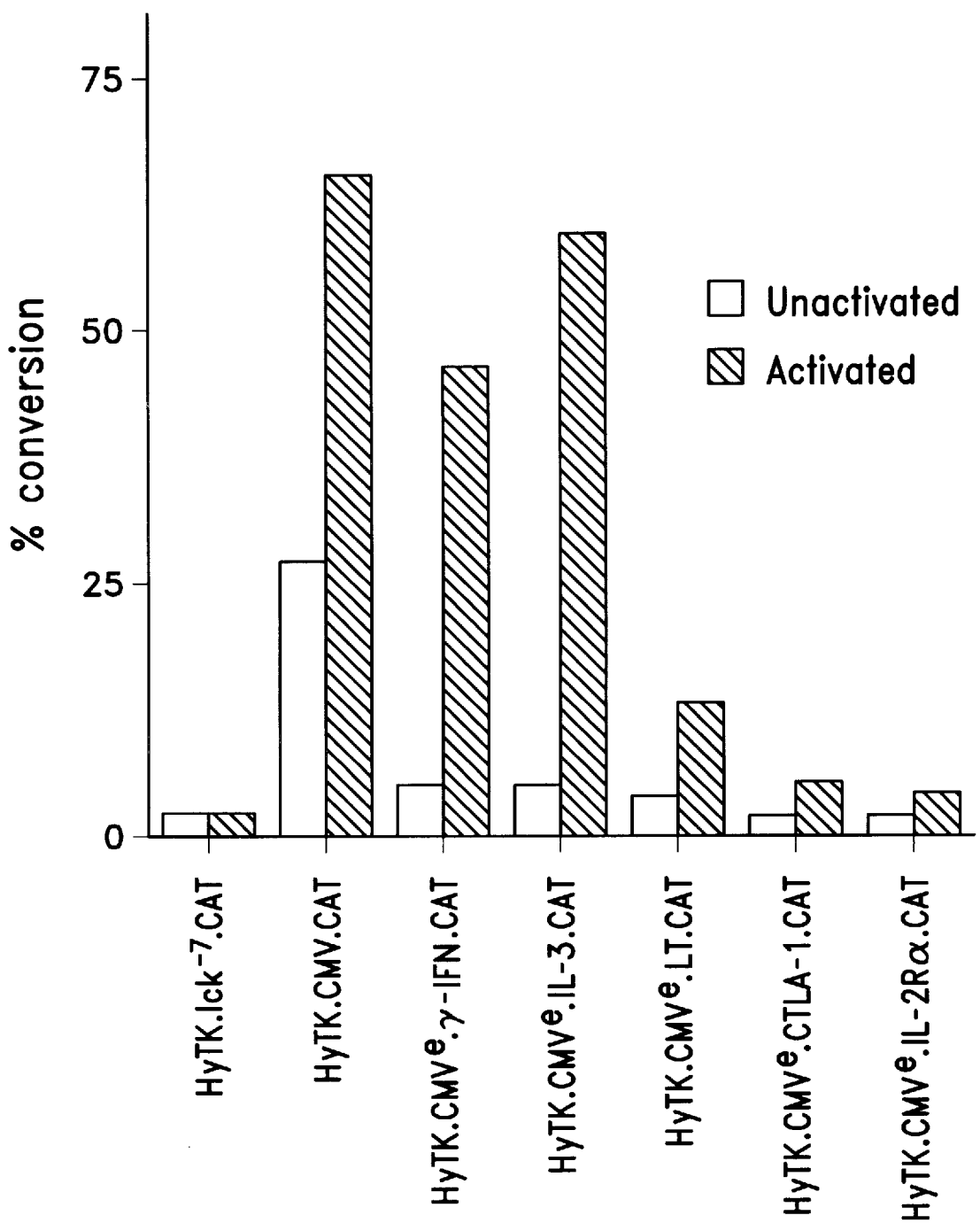
FIG. 21 is a bar graph depicting the level of CAT activity expressed by CD8+ human peripheral T lymphocytes transfected with the vectors listed, with or without activation of the cells, as described in Example 25.

As shown in FIG. 21, cells transfected with the negative control vector, HyTK.lck-7.CAT, and either left unactivated or activated did not express significant levels of CAT activity. Cells transfected with the positive control vector, HyTK.CMV.CAT, and left unactivated constitutively expressed CAT activity and the level of expression was increased upon T cell activation. Cells transfected with HyTK.CMVe.γ-IFN.CAT, HyTK.CMVe.IL-3.CAT or HyTK.CMVe.LT.CAT and left unactivated, did not express significant levels of CAT activity. However, cells transfected with HyTK.CMVe.γ-IFN.CAT, HyTK.CMVe.IL-3.CAT or HyTK.CMVe.LT.CAT expressed significant levels of CAT activity following activation for 24 h. Lower levels of activation-induced expression were also seen in cells transfected with HyTK.CMVe.CTLA-1.CAT or HyTK.CMVe.IL-2Rα.CAT.

The results demonstrate that the transcriptional control regions from γ-IFN, IL-3, LT, CTLA-1 and IL-2Rα, in combination with the CMV enhancer, mediate activation-induced expression in human CD8+ T lymphocytes. The results further demonstrate that the transcriptional control regions from γ-IFN, IL-3, LT, CTLA-1 and IL-2Rα, in combination with the CMV enhancer, are functional in human CD8+ T lymphocytes when inserted into a retroviral vector.

EXAMLE 26
Activation-induced expression in a retrovirally-infected human CMV-specific CD8+ cytotoxic T lymphocyte clone
Plasmids HyTK.CMV.CAT and HyTK.CMVe.LT.CAT were constructed as in Example 10. Plasmid HyTK.CMVe.γ-IFN.CAT was constructed as in Example 17.

Amphotropic PA317 producer clones were generated and characterized as in Example 17.

The CMV-specific human CD8+ cytotoxic T cell clone MRL 1A3 was generated from a volunteer CMV-seropositive donor using methods previously described (Riddell et al., 1991). This clone had a CD3+, CD8+, CD4– phenotype by FACS analysis and mediated class I MHC restricted cytolytic activity specific for autologous CMV-infected fibroblasts. MRL 1A3 was propagated by cyclical stimulation with autologous CMV-infected fibroblasts or anti-CD3 monoclonal antibody to provide T cell receptor stimulation and γ-irradiated feeder cells as previously described (Riddell and Greenberg, 1990).

Infection of CMV-reactive human CD8+ CTL clone MRL 1A3 was carried out as follows. For retroviral transduction, aliquots of 5×10$^5$ MRL 1A3 T cells were stimulated with anti-CD3 monoclonal antibody and γ-irradiated feeder cells, and the cultures supplemented with IL-2 at a concentration of 30 U/ml 1 d after stimulation. Three days after stimulation, the cells were exposed in a 1:1 vol/vol ratio to supernatants containing HyTK.CMV.CAT, HyTK.CMVe.γ-IFN.CAT, or HyTK.CMVe.LT.CAT retroviral particles. The culture medium was supplemented with polybrene at a concentration of 5 µg/ml and IL-2 at a concentration of 20 U/ml. One day after exposure to retrovirus supernatants (day 4 after stimulation), the T cells were washed and plated in fresh medium. On day 5, the cells were exposed to the retroviral supernatants for a second time under identical conditions to the day 3 infection. On day 6, the cells were washed and plated in culture medium containing hygromycin B at a concentration of 250 µg/ml and IL-2 at a concentration of 20 U/ml. On day 14, the remaining viable cells were restimulated with anti-CD3 monoclonal antibody and γ-irradiated feeder cells and propagated in the presence of hygromycin B at a concentration of 250 µg/ml. After the second cycle of hygromycin B selection, aliquots of each transduced culture were analyzed by Southern blotting to confirm successful transduction. The transduced cultures were propagated by cyclical stimulation with autologous CMV-infected fibroblasts or anti-CD3 monoclonal antibody to provide T cell receptor stimulation and γ-irradiated feeder cells as previously described (Riddell and Greenberg, 1990).

CAT extracts were prepared and assayed as follows. Aliquots (1×10$^4$ cells) of the transduced cells were plated in 30-ml of medium with 25×10$^6$ γ-irradiated PBL and 5×10$^6$ γ-irradiated EBV transformed LCL as feeder cells, and anti-CD3 monoclonal antibody to provide T cell receptor stimulation. The following day, the culture was supplemented with 25 U/ml of IL-2. After 4 d of culture, the cells were washed and resuspended in 30-ml of fresh medium containing 25 U/ml of IL-2. After a further 3 d of culture, the cells were washed again and resuspended in 30-ml of fresh medium containing 25 U/ml of IL-2. After 1–3 d, the cells were washed and resuspended at a density of 1×10$^6$ T cells/ml in fresh medium, and plated in 24-well plates at 1×10$^6$ T cells/well with 2×10$^6$ γ-irradiated PBL to rest. After 14 d of rest, cells were either harvested for CAT assay without activation, or were activated as follows: The transduced T cells were plated in 24-well plates at 5×10$^6$ T cells/well with 5×10$^6$ γ-irradiated PBL and 5×10$^5$ γ-irradiated EBV transformed LCL as feeder cells, and surface-bound anti-CD3 monoclonal antibody to provide T cell receptor stimulation. At 24 h, 48 h, or 96 h after activation, extracts were prepared for CAT assay. The cells were harvested and CAT extracts were prepared and assayed as described in Example 12, except that extracts were prepared in 60 µl of 0.25M Tris (pH 8.0).

Figure 22:
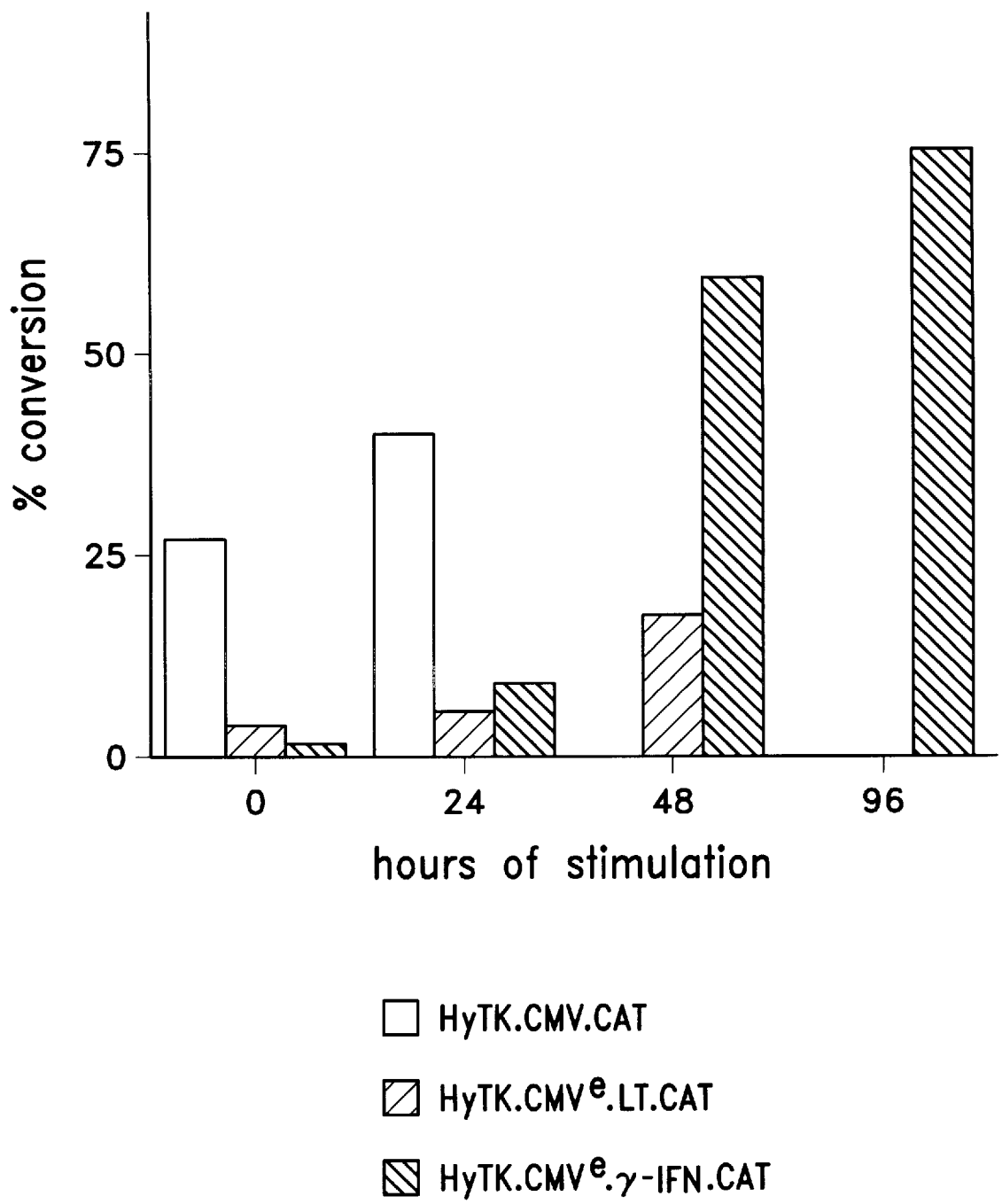
FIG. 22 is a bar graph depicting the time course of CAT activity expressed by the anti-CMV specific human cytotoxic T cell clone MRL 1A3 transfected with the vectors listed, with or without activation of the cells by cross-linking the T cell receptor using anti-CD3 antibody, as described in Example 26.

As shown in FIG. 22, cells infected with the positive control retroviral vector, HyTK.CMV.CAT, and left unactivated constitutively expressed CAT activity and the level of expression was increased upon T cell activation for 24 h. Cells infected with the HyTK.CMVe.LT.CAT retroviral vector and left unactivated, did not express significant levels of CAT activity. However, cells infected with the HyTK.CMVe.LT.CAT retroviral vector expressed significant levels of CAT activity at 48 h after activation. Cells infected with the HyTK.CMVe.γ-IFN.CAT retroviral vector and left unactivated, did not express significant levels of CAT activity. However, cells infected with the HyTK.CMVe.γ-IFN.CAT retroviral vector expressed significant levels of CAT activity at 48 h or 96 h after activation.

The results demonstrate that the γ-IFN transcriptional control region in combination with the CMV enhancer, or the LT transcriptional control region in combination with the CMV enhancer, mediate activation-induced expression in a CMV-reactive human CD8+ CTL clone. The results further demonstrate that the γ-IFN transcriptional control region in combination with the CMV enhancer, or the LT transcriptional control region in combination with the CMV enhancer, are functional in a CMV-reactive human CD8+ CTL clone when inserted into a retroviral vector and delivered via retroviral infection.

EXAMPLE 27

Growth of CMV-reactive human CD8+ CTL transduced with HyTK.CMVe.IL-3.IL-2, HvTK.CMVe.γ-IFN.IL-2, and HyTK.CMVe.IL-2Rα.IL-2 in the absence of exogenously added IL-2

The construction and proviral structure of the retroviral vector tgLS(+)HyTK is described fully in Lupton et al., 1991.

The proviral structure of the retroviral vector HyTK.CMVe.IL-3.IL-2 is arranged as depicted in FIG. 4D, where "TCR" represents the IL-3 transcriptional control region, "Gene" represents the human IL-2 cDNA, and "ENH" represents the CMV enhancer. Plasmid HyTK.CMVe.IL-3.IL-2 was constructed using standard techniques (Ausubel et al., 1987) as follows: A human IL-2 cDNA clone, which had been modified by placing a BamHI site at the 5' end and a SalI site at the 3' end, was inserted between the BamHI and SalI sites of HyTK.CMVe.IL-3.CAT (see Example 14) in place of the CAT gene.

The proviral structure of the retroviral vector HyTK.CMVe.γ-IFN.IL-2 is arranged as depicted in FIG. 4D, where "TCR" represents the γ-IFN transcriptional control region, "Gene" represents the human IL-2 cDNA, and "ENH" represents the CMV enhancer. Plasmid HyTK.CMVe.γ-IFN.IL-2 was constructed using standard techniques (Ausubel et al., 1987) as follows. Plasmid HyTK.γ-IFN.IL-2 was constructed first. This construct is a derivative of tgLS(+)HyTK (Lupton et al. 1991) containing nucleotides −541 to +128 of the human γ-IFN transcriptional control region (Ciccarone et al., 1990; Gray and Goeddel, 1982) linked to a human IL-2 cDNA inserted downstream of the HyTK gene, and an XhoI site immediately 5' of the human γ-IFN transcriptional control region. The XhoI-BstX1 fragment encompassing the CMV enhancer and the 5' portion of the γ-IFN transcriptional control region was then excised from tgCMVe.γ-IFN.CAT (as described in Example 17) and ligated between the XhoI and BstX1 sites of HyTK.γ-IFN.IL-2 to generate the construct designated HyTK.CMVe.γ-IFN.IL-2.

The proviral structure of the retroviral vector HyTK.CMVe.CTLA-1.IL-2 is arranged as depicted in FIG. 4D, where "TCR" represents the CTLA-1 transcriptional control region, "Gene" represents the human IL-2 cDNA, and "ENH" represents the CMV enhancer. Plasmid HyTK.CMVe.CTLA-1.IL-2 was constructed using standard techniques (Ausubel et al., 1987) as follows: A human IL-2 cDNA clone, which had been modified by placing a BamHI site at the 5' end and a SalI site at the 3' end, was inserted between the BamHI and SalI sites of HyTK.CMVe.CTLA-1.CAT (see Example 15) in place of the CAT gene.

The proviral structure of the retroviral vector HyTK.CMVe.IL-2Rα.IL-2 is arranged as depicted in FIG. 4D, where "TCR" represents the IL-2Rα transcriptional control region, "Gene" represents the human IL-2 cDNA, and "ENH" represents the CMV enhancer. Plasmid HyTK.CMVe.IL-2Rα.IL-2 was constructed using standard techniques (Ausubel et al., 1987) as follows: A human IL-2 cDNA clone, which had been modified by placing a BamHI site at the 5' end and a SalI site at the 3' end, was inserted between the BamHI and SalI sites of HyTK.CMVe.IL-2Rα.CAT (see Example 11) in place of the CAT gene.

PA317 amphotropic retrovirus producer clones were generated and characterized as in Example 17.

The CMV-specific human CD8+ cytotoxic T cell clone MRL 3C1I was generated as described in Example 26, and transduced with tgLS(+)HyTK, HyTK.CMVe.IL-3.IL-2, HyTK.CMVe.γ-IFN.IL-2. HyTK.CMVe.CTLA-1.IL-2, or HyTK.CMVe.IL-2Rα.IL-2 retroviral particles as described in Example 26.

As described below, the transduced CMV-specific human CD8+ CTL were grown in the absence of exogenous IL-2. Aliquots of the cultures transduced with tgL(S)(+)HyTK, HyTK.CMVe.IL-3.IL-2, HyTK.CMVe.γ-IFN.IL-2, HyTK.CMVe.CTLA-1.IL-2, or HyTK.CMVe.IL-2Rα.IL-2 were plated in 24 well plates at $1\times10^6$ T cells/well with $1\times10^5$ autologous fibroblasts infected with AD169 strain CMV to provide antigen stimulation, and $1\times10^6$ γ-irradiated PBL and $1\times10^5$ γ-irradiated EBV transformed LCL as feeder cells. Exogenous IL-2 was not added to the cultures. After 7 days, cells were harvested and viable cell numbers determined by trypan blue exclusion. The T cells were then replated in 24well plates under identical restimulation conditions. After an additional 7 days, viable cell numbers were again determined by trypan blue exclusion.

Figure 23:
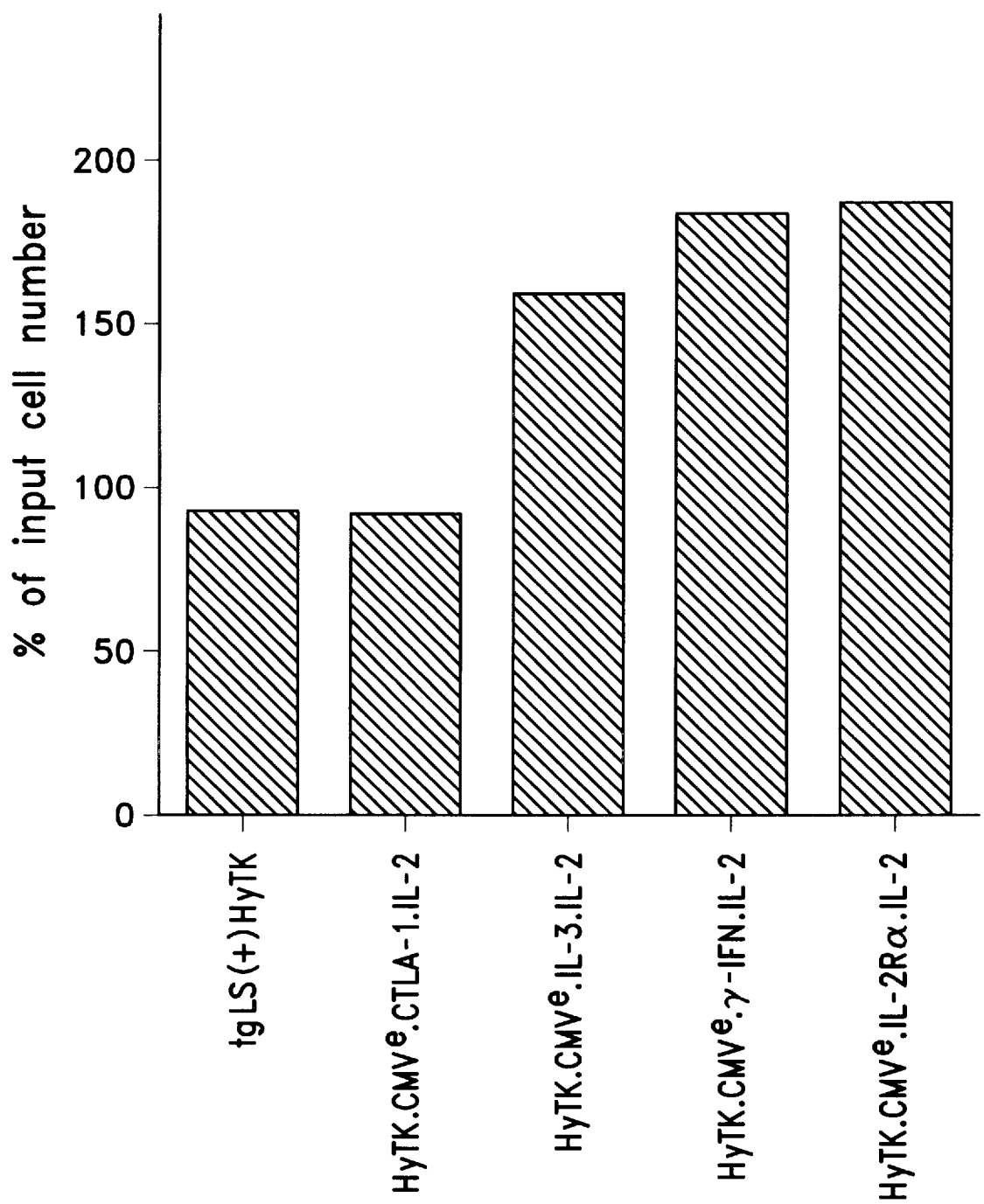
FIG. 23 is a bar graph depicting the growth of anti-CMV specific human cytotoxic T cell clone MRL 1A3 after transduction with a control vector or a vector encoding IL-2. The cells were grown in the absence of exogenous IL-2, but in the presence of autologous fibroblasts infected with AD169 strain CMV to provide antigen stimulation. The data represent the cumulative changes in cell number over two 7 day stimulation cycles, as described in Example 27.

The data shown in FIG. 23 represent the cumulative changes in cell numbers over the two 7 day stimulation cycles. The results demonstrate that relative to cells transduced with the control tgLS(+)HyTK vector, cells transduced with HyTK.CMVe.IL-3.IL-2, HyTK.CMVe.γ-IFN.IL-2, and HyTK.CMVe.IL-2Rα.IL-2 were able to proliferate in the absence of exogenously added IL-2.

Utility

The vectors of the current invention are useful in creating lymphocytes, particularly antigen-specific CTLS, that have a lessened dependency on TH cells and/or stimulatory factors provided by the TH cells, for example, cytokines. The cells containing the vectors, particularly the CTLs with lessened dependency on TH cells caused by expression of the stimulatory factor encoded in the vector, are useful for adoptive transfer therapy to modulate the immune response.

We claim:

1. A recombinant polynucleotide comprising a region encoding a stimulators polypeptide that stimulates lymphocyte proliferation operably linked to a heterologous transcriptional control region, wherein the transcriptional control region causes activation-induced expression of the stimulatory factor encoding region when present in a lymphocyte that has been activated, wherein the stimulatory factor is IL-2 and wherein expression of the stimulatory factor polypeptide in the activated lymphocyte reduces dependency of the lymphocyte on T helper cells ($T_H$ cells) for proliferation.

2. The recombinant polynucleotide of claim 1 in the form of a recombinant expression vector.

3. The recombinant vector of claim 2, wherein said recombinant vector is selected from the group consisting of retroviral vectors, AAV vectors and non-viral vectors.

4. The recombinant vector of claim 3 wherein the transcriptional control region comprises a promoter derived from a cytokine gene that exhibits activation-induced expression in lymphocytes.

5. The recombinant vector of claim 1 wherein the lymphocytes are CD8+ cytotoxic T lymphocytes.

6. The recombinant vector of claim 5 wherein the transcriptional control region is derived from a gene selected from the group consisting of an IL-3 gene, an IL-4 gene, a γ-IFN gene and a GM-CSF gene.

7. The recombinant vector of claim 3 wherein the transcriptional control region comprises a promoter selected from the group consisting of promoters for CTLA-1, γ-IFN, IL2Rα, IL-3, IL-4 and LT.

8. The recombinant vector of claim 7 wherein the transcriptional control region further comprises an enhancer.

9. The recombinant vector of claim 8 wherein the enhancer is an HCMV IE94 enhancer.

10. The recombinant vector of claim 2 further comprising a region encoding a positive selectable marker.

11. The recombinant vector of claim 2 further comprising a region encoding a negative selectable marker.

12. The recombinant vector of claim 2 further comprising a region encoding a negative selectable marker fused to a positive selectable marker.

13. A host cell transformed with the recombinant vector of claim 5, and progeny thereof wherein the progeny expresses the same characteristics as the parent transformed host cell obtained by proliferation of the transformed host cell.

14. The host cell and progeny thereof of claim 13 wherein the cell is a CD8+ CTL.

15. A method of preparing a transformed lymphocyte, comprising transforming a lymphocyte with the polynucleotide of claim 1, wherein as a result of the transformation the lymphocyte is rendered of lessened dependency on $T_H$ cells for proliferation.

16. A method of preparing a transformed CTL, comprising transforming a CD8+ CTL with the vector of claim 5, wherein as a result of the transformation the CTL is rendered of lessened dependency on $T_H$ cells for proliferation.

17. A cell produced by the method of claim 15, and progeny thereof obtained by proliferation of the produced cell.

18. A cell produced by the method of claim 16, and progeny thereof wherein the progeny expresses the same characteristics as the parent transformed host cell obtained by proliferation of the produced cell.

* * * * *

UNITED STATES PATENT AND TRADEMARK OFFICE
CERTIFICATE OF CORRECTION

PATENT NO. : 5,874,556
DATED : February 23, 1999
INVENTOR(S) : Stephen D. Lupton *et al.*

It is certified that error appears in the above-identified patent and that said Letters Patent is hereby corrected as shown below:

In claim 1, line 2, "stimulators" should read "stimulatory,".

In claim 5, line 1, "claim 1" should read "claim 4".

Signed and Sealed this

Third Day of August, 1999

Attest:

Attesting Officer

Q. TODD DICKINSON

*Acting Commissioner of Patents and Trademarks*